United States Patent
Nebrigic et al.

(10) Patent No.: US 8,506,506 B2
(45) Date of Patent: Aug. 13, 2013

(54) TISSUE TREATMENT APPARATUS WITH FUNCTIONAL MECHANICAL STIMULATION AND METHODS FOR REDUCING PAIN DURING TISSUE TREATMENTS

(75) Inventors: Dragan D. Nebrigic, Carlsbad, CA (US); Herb Lara, Newark, CA (US); Richard Hatch, Pleasanton, CA (US); Igor Leonidovich Tchertkov, Walnut Creek, CA (US); Kai Nakamura, San Mateo, CA (US); Laura England, Alameda, CA (US); Marlo Cinco, Castro Valley, CA (US)

(73) Assignee: Solta Medical, Inc., Hayward, CA (US)

( * ) Notice: Subject to any disclaimer, the term of this patent is extended or adjusted under 35 U.S.C. 154(b) by 565 days.

(21) Appl. No.: 12/649,781

(22) Filed: Dec. 30, 2009

(65) Prior Publication Data

US 2010/0179455 A1 Jul. 15, 2010

Related U.S. Application Data

(60) Provisional application No. 61/226,140, filed on Jul. 16, 2009, provisional application No. 61/143,957, filed on Jan. 12, 2009.

(51) Int. Cl.
*A61H 1/00* (2006.01)
*A61H 1/02* (2006.01)
*A61H 5/00* (2006.01)

(52) U.S. Cl.
USPC ............................................. 601/15; 607/100

(58) Field of Classification Search
USPC .................. 607/1, 2, 96, 100, 101; 601/15, 601/46, 84, 89, 97; 606/33
See application file for complete search history.

(56) References Cited

U.S. PATENT DOCUMENTS

| | | | |
|---|---|---|---|
| 3,861,383 | A | 1/1975 | Kovach |
| 4,014,347 | A | 3/1977 | Halleck et al. |
| 4,595,008 | A | 6/1986 | Guibert |
| 5,447,530 | A | 9/1995 | Guibert et al. |
| 5,449,378 | A | 9/1995 | Schouenborg |

(Continued)

FOREIGN PATENT DOCUMENTS

| | | |
|---|---|---|
| AU | 779100 B2 | 9/2000 |
| CA | 2364098 A1 | 9/2000 |

(Continued)

OTHER PUBLICATIONS

Junger, M. et al., "Local therapy and treatment costs of chronic, venous leg ulcers with electrical stimulation (Dermapulse): a prospective, placebo controlled, double blind trial", Wound Rep Reg (2008) 480-487.

(Continued)

*Primary Examiner* — Theodore Stigell
(74) *Attorney, Agent, or Firm* — Wood, Herron & Evans, LLP

(57) ABSTRACT

Apparatus and methods for delivering electromagnetic energy to a patient's tissue with a reduction in the pain experienced by the patient. The tissue treatment apparatus includes a delivery device configured to transfer electromagnetic energy through the skin surface to a region of tissue and a vibration device mechanically coupled with the delivery device. The vibration device is configured to transfer mechanical vibrations through the skin surface to the region of tissue.

11 Claims, 14 Drawing Sheets

(56) References Cited

U.S. PATENT DOCUMENTS

| | | | |
|---|---|---|---|
| 5,580,350 A | 12/1996 | Guibert et al. | |
| 5,660,836 A | 8/1997 | Knowlton | |
| 5,727,556 A | 3/1998 | Weth et al. | |
| 5,755,753 A | 5/1998 | Knowlton | |
| 5,871,524 A | 2/1999 | Knowlton | |
| 5,919,219 A | 7/1999 | Knowlton | |
| 5,941,902 A | 8/1999 | Holcomb | |
| 5,948,009 A * | 9/1999 | Tu | 607/96 |
| 5,948,011 A | 9/1999 | Knowlton | |
| 6,011,994 A | 1/2000 | Kronberg | |
| 6,063,079 A | 5/2000 | Hovda et al. | |
| 6,068,596 A | 5/2000 | Weth et al. | |
| 6,086,585 A | 7/2000 | Hovda et al. | |
| 6,091,989 A | 7/2000 | Swerdlow et al. | |
| 6,091,994 A | 7/2000 | Loos | |
| 6,109,268 A | 8/2000 | Thapliyal et al. | |
| 6,139,545 A | 10/2000 | Utley et al. | |
| 6,210,402 B1 | 4/2001 | Olsen et al. | |
| 6,217,534 B1 | 4/2001 | Natalicio | |
| 6,228,078 B1 | 5/2001 | Eggers et al. | |
| 6,254,600 B1 | 7/2001 | Willink et al. | |
| 6,264,652 B1 | 7/2001 | Eggers et al. | |
| 6,296,638 B1 | 10/2001 | Davison et al. | |
| 6,309,387 B1 | 10/2001 | Eggers et al. | |
| 6,311,090 B1 | 10/2001 | Knowlton | |
| 6,387,380 B1 | 5/2002 | Knowlton | |
| 6,405,090 B1 | 6/2002 | Knowlton | |
| 6,408,212 B1 | 6/2002 | Neev | |
| 6,413,255 B1 | 7/2002 | Stern | |
| 6,432,103 B1 | 8/2002 | Ellsberry et al. | |
| 6,445,955 B1 | 9/2002 | Michelson et al. | |
| 6,453,202 B1 | 9/2002 | Knowlton | |
| 6,461,350 B1 | 10/2002 | Underwood et al. | |
| 6,461,354 B1 | 10/2002 | Olsen et al. | |
| 6,535,767 B1 | 3/2003 | Kronberg | |
| 6,544,261 B2 | 4/2003 | Ellsberry et al. | |
| 6,572,594 B2 | 6/2003 | Satterfield et al. | |
| 6,659,106 B1 | 12/2003 | Hovda et al. | |
| 6,679,908 B2 * | 1/2004 | Shimizu | 607/109 |
| 6,697,670 B2 | 2/2004 | Chomenky et al. | |
| 6,719,754 B2 | 4/2004 | Underwood et al. | |
| 6,746,447 B2 | 6/2004 | Davison et al. | |
| 6,766,202 B2 | 7/2004 | Underwood et al. | |
| 6,832,996 B2 | 12/2004 | Woloszko et al. | |
| 6,896,672 B1 | 5/2005 | Eggers et al. | |
| 6,902,554 B2 | 6/2005 | Huttner | |
| 6,920,883 B2 | 7/2005 | Bessette et al. | |
| 6,930,590 B2 | 8/2005 | Ling et al. | |
| 6,949,096 B2 | 9/2005 | Davison et al. | |
| 6,991,631 B2 | 1/2006 | Woloszko et al. | |
| 7,004,941 B2 | 2/2006 | Tvinnereim et al. | |
| 7,020,528 B2 | 3/2006 | Neev | |
| 7,117,034 B2 | 10/2006 | Kronberg | |
| 7,131,969 B1 | 11/2006 | Hovda et al. | |
| 7,241,293 B2 | 7/2007 | Davison | |
| 7,331,957 B2 | 2/2008 | Woloszko et al. | |
| 7,389,145 B2 | 6/2008 | Kilgore et al. | |
| 7,452,358 B2 | 11/2008 | Stern et al. | |
| 7,473,251 B2 | 1/2009 | Knowlton et al. | |
| 7,762,964 B2 | 7/2010 | Slatkine | |
| 7,762,965 B2 | 7/2010 | Slatkine | |
| 8,287,579 B2 | 10/2012 | Nimitz | |
| 2001/0025176 A1 | 9/2001 | Ellsberry et al. | |
| 2002/0087155 A1 | 7/2002 | Underwood et al. | |
| 2002/0133149 A1 | 9/2002 | Bessette | |
| 2002/0193789 A1 | 12/2002 | Underwood et al. | |
| 2003/0117371 A1 | 6/2003 | Roberts et al. | |
| 2003/0208194 A1 | 11/2003 | Hovda et al. | |
| 2003/0212351 A1 | 11/2003 | Hissong et al. | |
| 2003/0212396 A1 | 11/2003 | Eggers et al. | |
| 2003/0225403 A1 | 12/2003 | Woloszko et al. | |
| 2004/0098065 A1 | 5/2004 | Hagglof et al. | |
| 2004/0127895 A1 | 7/2004 | Flock et al. | |
| 2004/0206365 A1 | 10/2004 | Knowlton | |
| 2004/0210214 A1 | 10/2004 | Knowlton | |
| 2005/0152905 A1 | 7/2005 | Omoigui | |
| 2005/0217682 A1 | 10/2005 | Orton | |
| 2005/0234439 A1 | 10/2005 | Underwood | |
| 2005/0267454 A1 | 12/2005 | Hissong et al. | |
| 2005/0288665 A1 | 12/2005 | Woloszko | |
| 2006/0004306 A1 | 1/2006 | Altshuler et al. | |
| 2006/0036300 A1 | 2/2006 | Kreindel | |
| 2006/0089688 A1 | 4/2006 | Panescu | |
| 2006/0171890 A1 | 8/2006 | Yeomans et al. | |
| 2006/0212077 A1 | 9/2006 | Pilla et al. | |
| 2006/0217636 A1 | 9/2006 | Braig et al. | |
| 2006/0293722 A1 | 12/2006 | Slatkine et al. | |
| 2007/0010811 A1 | 1/2007 | Stern et al. | |
| 2007/0060921 A1 | 3/2007 | Janssen et al. | |
| 2007/0078290 A1 | 4/2007 | Esenaliev | |
| 2007/0093797 A1 | 4/2007 | Chan et al. | |
| 2007/0093798 A1 | 4/2007 | DeBenedictis et al. | |
| 2007/0142863 A1 | 6/2007 | Bradley | |
| 2007/0167943 A1 | 7/2007 | Janssen et al. | |
| 2007/0219604 A1 | 9/2007 | Yaroslavsky et al. | |
| 2007/0219605 A1 | 9/2007 | Yaroslavsky et al. | |
| 2007/0282318 A1 | 12/2007 | Spooner et al. | |
| 2008/0015565 A1 | 1/2008 | Davison | |
| 2008/0015568 A1 | 1/2008 | Paul et al. | |
| 2008/0058784 A1 | 3/2008 | Manstein et al. | |
| 2008/0091179 A1 | 4/2008 | Durkin et al. | |
| 2008/0119828 A1 | 5/2008 | Nelson et al. | |
| 2008/0188779 A1 | 8/2008 | Vallero | |
| 2008/0200969 A1 | 8/2008 | Weber | |
| 2008/0215039 A1 | 9/2008 | Slatkine et al. | |
| 2008/0288035 A1 | 11/2008 | Gill et al. | |
| 2008/0294226 A1 | 11/2008 | Moffitt et al. | |
| 2008/0306418 A1 | 12/2008 | DeBenedictis et al. | |
| 2009/0076572 A1 | 3/2009 | Nimitz | |
| 2009/0149930 A1 | 6/2009 | Schenck | |
| 2009/0171424 A1 * | 7/2009 | Britva et al. | 607/101 |
| 2009/0270954 A1 | 10/2009 | Schenck | |
| 2009/0287207 A1 | 11/2009 | Stern et al. | |
| 2010/0145321 A1 | 6/2010 | Altshuler et al. | |
| 2010/0179455 A1 | 7/2010 | Nebrigic et al. | |
| 2010/0179531 A1 | 7/2010 | Nebrigic et al. | |
| 2011/0015687 A1 | 1/2011 | Nebrigic et al. | |
| 2011/0172586 A1 | 7/2011 | Hennings et al. | |
| 2011/0202048 A1 | 8/2011 | Nebrigic | |

FOREIGN PATENT DOCUMENTS

| | | |
|---|---|---|
| EP | 1158919 | 12/2001 |
| EP | 1407720 A1 | 4/2004 |
| JP | 11504828 | 5/1999 |
| JP | 2007268297 A | 10/2007 |
| JP | 2002537939 | 6/2008 |
| WO | 9634568 A1 | 11/1996 |
| WO | 0053113 | 9/2000 |
| WO | 2008069647 A1 | 6/2008 |

OTHER PUBLICATIONS

Kim YH et al., "Effect of pulsed radiofrequency for postherpetic neuralgia", Acta Anaesthesiol Scand 2008; 52: 1140-1143, Singapore.
Van Zundert, J. et al., "Pulsed radiofrequency adjacent to the cervical dorsal root ganglion in chronic cervical radicular pain: a double blind sham controlled randomized clinical trial", Pain 127 (2007) 173-182.
Rosted P. et al., "Use of Stimulation techniques in pain treatment", Ugeskr Laeger. May 15, 2006; 168(20):1982-6 (abstract only of Danish article).
Apkarian, AV et al., "Heat-induced pain diminishes vibrotactile perception: a touch gate", Somatosensory and Motor Research, vol. 11, No. 3, 1994, pp. 259-267.
Pevzner et al., "Pulsed radiofrequency treatment of severe radicular pain", Harefuah. Mar. 2005;144(3):178-80, 231. (article in Hebrew).
Mikeladze et al, "Pulsed radiofrequency application in treatment of chronic zygapophyseal joint paint", The Spine Journal 3 (2003) 360-362.
Fisher GH et al., "Concurrent use of a handheld forced cold air device minimizes pteient discomfort during fractional photothermolysis", Dermatol Surg 2005, 31:1242-1244.

Maeda Y. et al, "Low frequencies, but not high frequencies of bi-polar spinal cord stimulation reduce cutaneous and muscle hyperalgesia induced by nerve injury", Pain 138 (2008) 143-152.

Rottmann S. et al, "Electrical low-frequency stimulation induces homotopic long-term depression of nociception and pain from hand in man", Clinical Neurophysiology 119 (2008) 1895-1904.

Gold, MH, "Treatment of wrinkles and elastosis using vacuum-assisted bipolar radiofrequency heating of the dermis", Dermatol Surg 2007; 33:300-309.

Gildenberg, PL "History of electrical neuromodulation for chronic pain", Pain Medicine, vol. 7, No. S1, 2006.

Ersek, RA, "Transcutaneous electrical neurostimulation: a new therapeutic modality for controlling pain", Clinical Orthopaedics and Related Research, Oct. 1977, vol. 128, 314-324, Section II: General Orthopaedics.

Fletcher, H. "Painless Depo-medroxyprogresterone acetate (DMPA) injections using the 'pinch technique'" Journal of Obstetrics and Gynaecology (Aug. 2004) vol. 24, No. 5, 562-563.

Saijo, M. et al., "Lack of pain reduction by a vibrating local anesthetic attachment: a pilot study" Anesth Prog 52:62-64 2005.

USPTO, Office Action issued in related U.S. Appl. No. 12/134,009 dated Mar. 1, 2012.

Ersek, "Transcutaneous Electrical Neurostimulation: A New Therapeutic Modality for Controlling Pain," Clin. Ortop. Relat. Res., 1977, 128:314-24.

Fletcher, "Painless Depo-Medroxyprogesterone Acetate (DMPA) Injections Using the 'Pinch Technique,'" J. Obstet. Gynaecol., 2004, 24(5):562-3.

International Search Report and Written Opinion, PCT/US08/65983, Oct. 1, 2008, 9 pages.

Saijo et al., "Lack of Pain Reduction by a Vibrating Local Anesthetic Attachment: A Pilot Study," Aneth. Prog., 2005, 52(2):62-4.

U.S. Appl. No. 60/942,175, filed Jun. 5, 2007, Leonard C. DeBenedictis (not enclosed).

USPTO, Office Action issued in related U.S. Appl. No. 12/823,214 dated Jul. 23, 2012.

USPTO, Office Action issued in related U.S. Appl. No. 12/134,009 dated Aug. 21, 2012.

Evans, Jeff, "Match Vein Tx to Patient Preference, Tolerance", Dec. 2005, Skin and Allergy News, pp. 16-17.

USPTO, Office Action issued in related U.S. Appl. No. 12/823,544 dated Jan. 18, 2013.

USPTO, Office Action issued in related U.S. Appl. No. 12/823,214 dated Jan. 31, 2013.

* cited by examiner

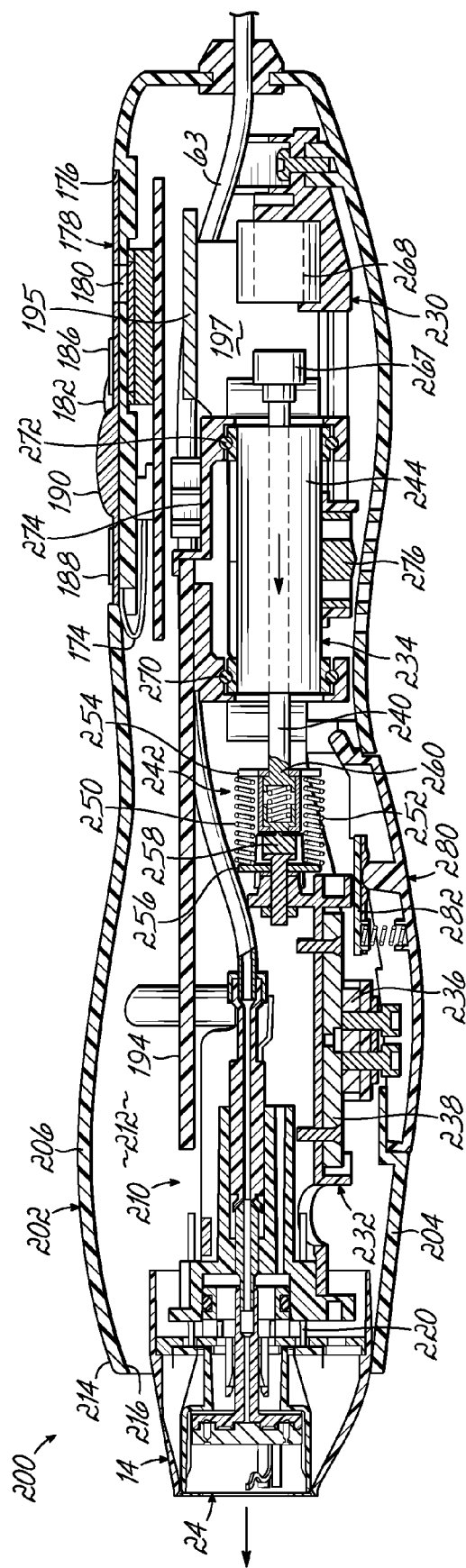
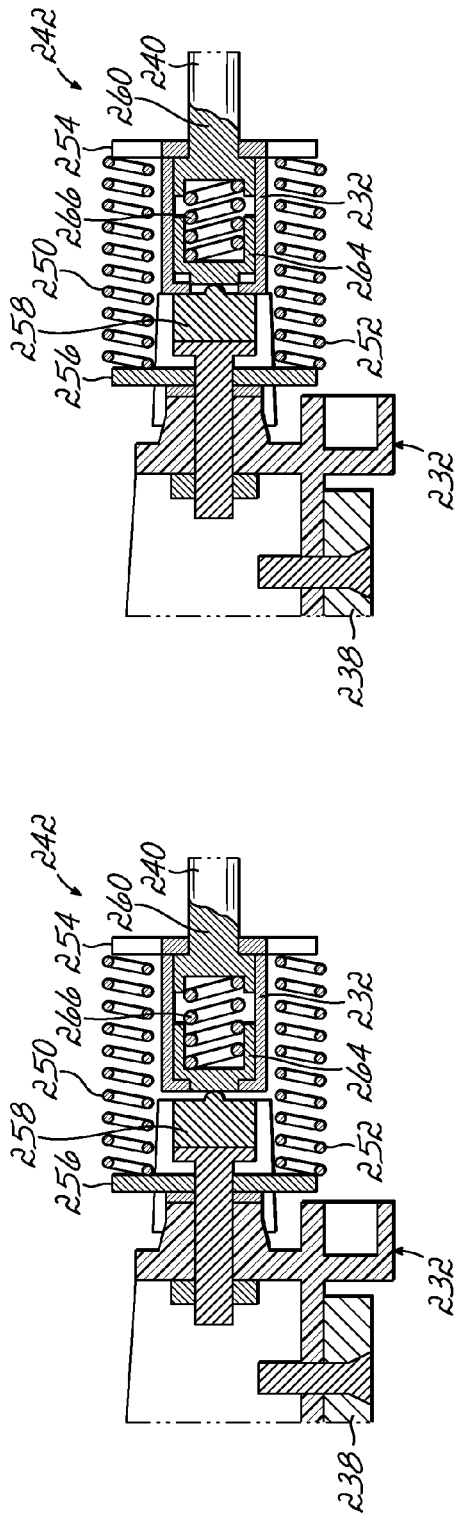
FIG. 18
FIG. 18A
FIG. 19A

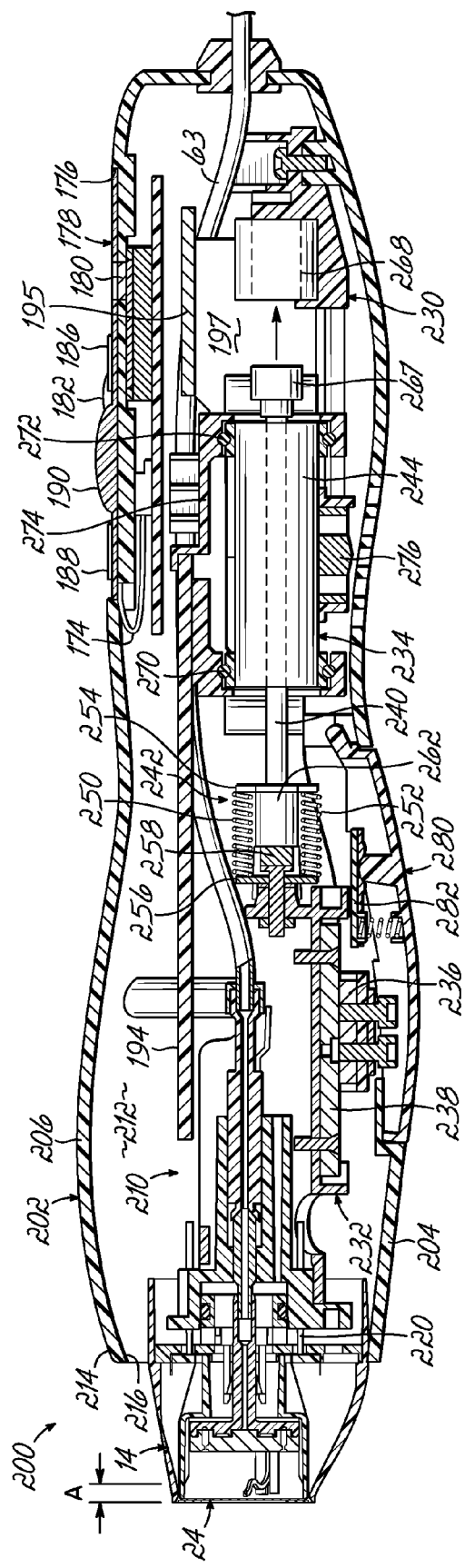
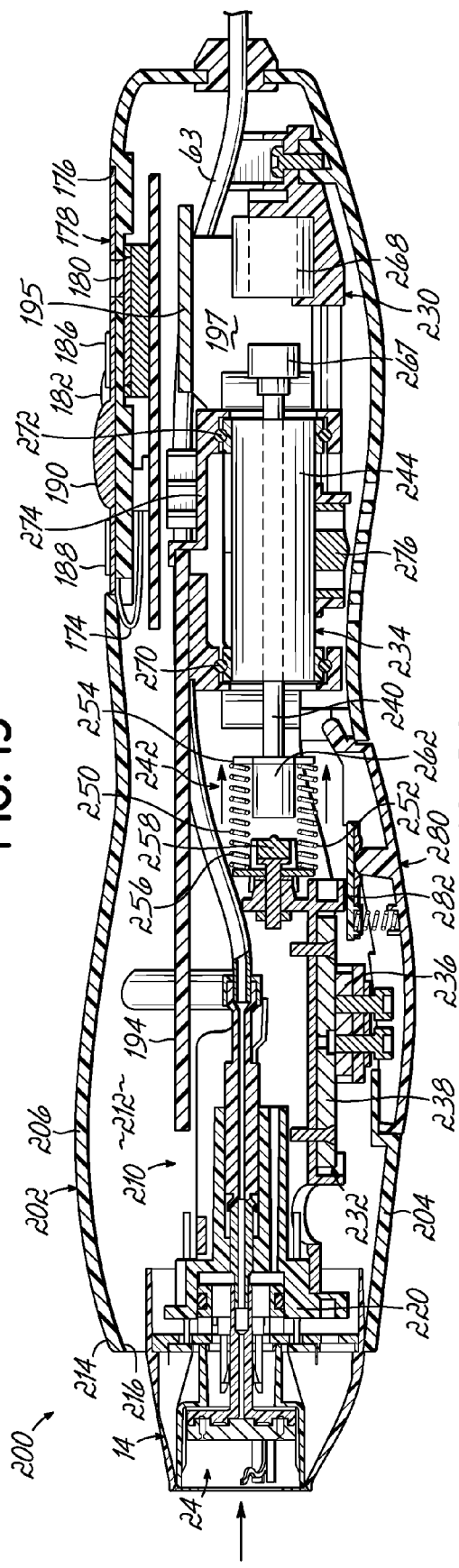
FIG. 19
FIG. 20

TISSUE TREATMENT APPARATUS WITH FUNCTIONAL MECHANICAL STIMULATION AND METHODS FOR REDUCING PAIN DURING TISSUE TREATMENTS

CROSS-REFERENCE TO RELATED APPLICATIONS

This Application claims the benefit of Application No. 61/143,957, filed Jan. 12, 2009 and claims the benefit of Application No. 61/226,140, filed Jul. 16, 2009, which are hereby incorporated by reference herein in their entirety.

BACKGROUND

The invention generally relates to apparatus and methods for treating tissue with high frequency energy and, more particularly, relates to treatment apparatus and methods for reducing patient pain with functional mechanical stimulation while treating tissue with high frequency energy.

Various cosmetic tissue treatments use energy delivery devices to non-invasively and non-ablatively treat tissue in order to improve a patient's appearance, such as smoothing and tightening skin; contouring along the jaw line and under the chin, and improving skin texture; softening wrinkles around the mouth, eyes and forehead; reducing cellulite; or removing skin spots or hair. These non-invasive, transcutaneous procedures involve no surgery or injections but instead project electromagnetic energy into the tissue. Such non-invasive energy delivery devices may emit the electromagnetic energy in different regions of the electromagnetic spectrum to accomplish the tissue treatment with reduced patient recovery time in comparison with ablative procedures.

Skin is a type of body tissue that includes plural distinct layers. The epidermis constitutes the visible outer layer on the surface. The dermis, which underlies the epidermis, contains collagen fibers, blood vessels, hair follicles, and other skin components. The hypodermis or subcutaneous fat layer, which underlies the dermis, consists of fat tissue and a web of collagen fibers in the form of fibrous septae running through the fat. The fibrous septae secure the dermis to the underlying bone and muscle. Collagen fibers are recognized to be a very flexible and stretchable protein and are characterized by a high tensile strength.

The occurrence of wrinkles is an unavoidable natural process. Wrinkles are primarily associated with advancing age and skin damage arising from exposure to damaging environmental factors. Environmental factors include sun damage from exposure to sunlight, air pollution, smoking, repetitive facial movements such as frowning, and the natural effects of gravity, which cause sagging of the skin with advancing aging. Deteriorating collagen exhibits a loss of elasticity, which results in the formation of rhytids or wrinkling of the epidermis.

Electromagnetic radiation, specifically light and heat, applied to the different layers of the skin can have a physiological effect on the skin's appearance. In particular, electromagnetic energy can arrest the formation of wrinkles and impart a more youthful skin appearance. High frequency treatment devices, such as radio-frequency (RF)-based treatment devices, may be used to treat skin tissue non-ablatively and non-invasively with heat. Such high frequency devices operate by transmitting high frequency energy through the epidermis to the underlying tissue, while actively cooling the epidermis to prevent thermal damage to a depth of the skin tissue near the skin surface. The high frequency energy heats the tissue at depths beneath the cooled region to a therapeutic temperature sufficient to denature the collagen, which causes the collagen fibers in the dermis to shrink and contract. In addition to the tightening of the treated tissue as the collagen fibers contract, treatment with high frequency energy also causes a mild inflammation. The inflammatory response of the treated tissue may cause new collagen to be generated over time, which can result in additional tissue contraction. When the inflammatory response of the treated tissue is highly significant, the new collagen formed is known as scar collagen.

Conventional high frequency treatment devices employ a handpiece, a disposable treatment tip coupled with a nose of the handpiece, and a high frequency generator connected by conductors inside the handpiece with an electrode in the treatment tip. Conventional electrodes consist of a pattern of one or more metallic features carried on a flexible electrically insulating substrate, such as a thin film of polyimide. The substrate contacts the patient's skin surface during treatment and the metallic features reside on the non-contact side of the substrate. The temperature of the treatment tip, which is measured by temperature sensors carried on the treatment tip, is correlated with the temperature of the patient's skin During the procedure, the doctor controls the energy density of the high frequency power delivered from the electrode with a treatment setting. Treatment tips are frequently intended for single patient use and, therefore, are not reusable. Following the patient treatment, the doctor or treatment technician removes the treatment tip from the handpiece and, if disposable, discards it.

Patient pain is inherent in tissue treatments using electromagnetic energy. Patient pain is typically regulated to optimize the treatment result while also minimizing patient discomfort to make the procedure tolerable. A patient may be given an oral pain medication and/or a local topical anesthesia cream may be applied as a numbing agent. At the inception of the treatment procedure, the doctor will initially administer the high frequency energy at a treatment setting to one or more test sites and monitor patient feedback on the heat sensation associated with the treatment setting being used. A tolerable, yet comfortable, treatment setting for the treatment procedure is established based upon the patient feedback from the test sites.

The treatment electrode used in the treatment includes a conductor region delimited by an outer peripheral edge. For monopolar energy delivery, an edge effect has been observed at the outer peripheral edge that causes the energy density of the high frequency energy delivered to the tissue to be non-uniform across the surface area of the treatment electrode. Specifically, the energy density is highest near the peripheral edge of the electrode. As a result, tissue proximate to the outer peripheral edge of the electrode is heated to a higher temperature than tissue proximate to the interior surface area of the electrode. The higher temperatures near the peripheral edge form hot spot thermal zones that are a highly likely source of heat-related pain perceived by the patient. Because patient discomfort is linked with the treatment setting, reducing the treatment level to counteract the edge effect effectively reduces the average energy density for the high frequency energy delivered during the treatment procedure.

In general, the results and the chance for pain or discomfort scale with the treatment setting used by the doctor. What is needed, therefore, are apparatus and methods for reducing the pain associated with such tissue treatments so that patient discomfort is alleviated and therapeutic results can be improved by increasing the treatment setting.

SUMMARY OF THE INVENTION

The embodiments of the invention are generally directed to apparatus and methods for transcutaneously delivering electromagnetic energy to treat tissue underlying a skin surface, particularly during non-invasive and non-ablative therapeutic tissue treatments, with reduced patient pain.

In one embodiment, a tissue treatment apparatus is provided for use in treating a region of tissue located beneath a skin surface with electromagnetic energy. The tissue treatment apparatus includes a delivery device configured to transfer the electromagnetic energy through the skin surface to the region of tissue and a vibration device mechanically coupled with the delivery device. The vibration device is configured to transfer mechanical vibrations through the skin surface to the region of tissue. The mechanical vibrations reduce patient discomfort (i.e., pain) associated with treatment and, in particular, treatment with electromagnetic energy that heats the targeted tissue.

In another embodiment, a method is provided for operating a tissue treatment apparatus to treat a region of tissue located beneath a skin surface with electromagnetic energy. The method includes delivering the electromagnetic energy through the skin surface to the region of tissue and transferring mechanical vibrations through the skin surface and into the region of tissue. The mechanical vibrations reduce patient discomfort (i.e., pain) associated with treatment and, in particular, treatment with electromagnetic energy that heats the targeted tissue.

BRIEF DESCRIPTION OF THE DRAWINGS

FIG. 18 is a cross-sectional view of the handpiece taken generally along line 18-18 in FIG. 16.

FIG. 18A is an enlarged view of a portion of FIG. 18.

FIGS. 19 and 20 are cross-sectional views similar to FIG. 18 illustrating the operation of the treatment system to use the vibration device to move the treatment tip relative to the skin surface of the patient.

FIG. 19A is an enlarged view of a portion of FIG. 19.

DETAILED DESCRIPTION

Figure 1:
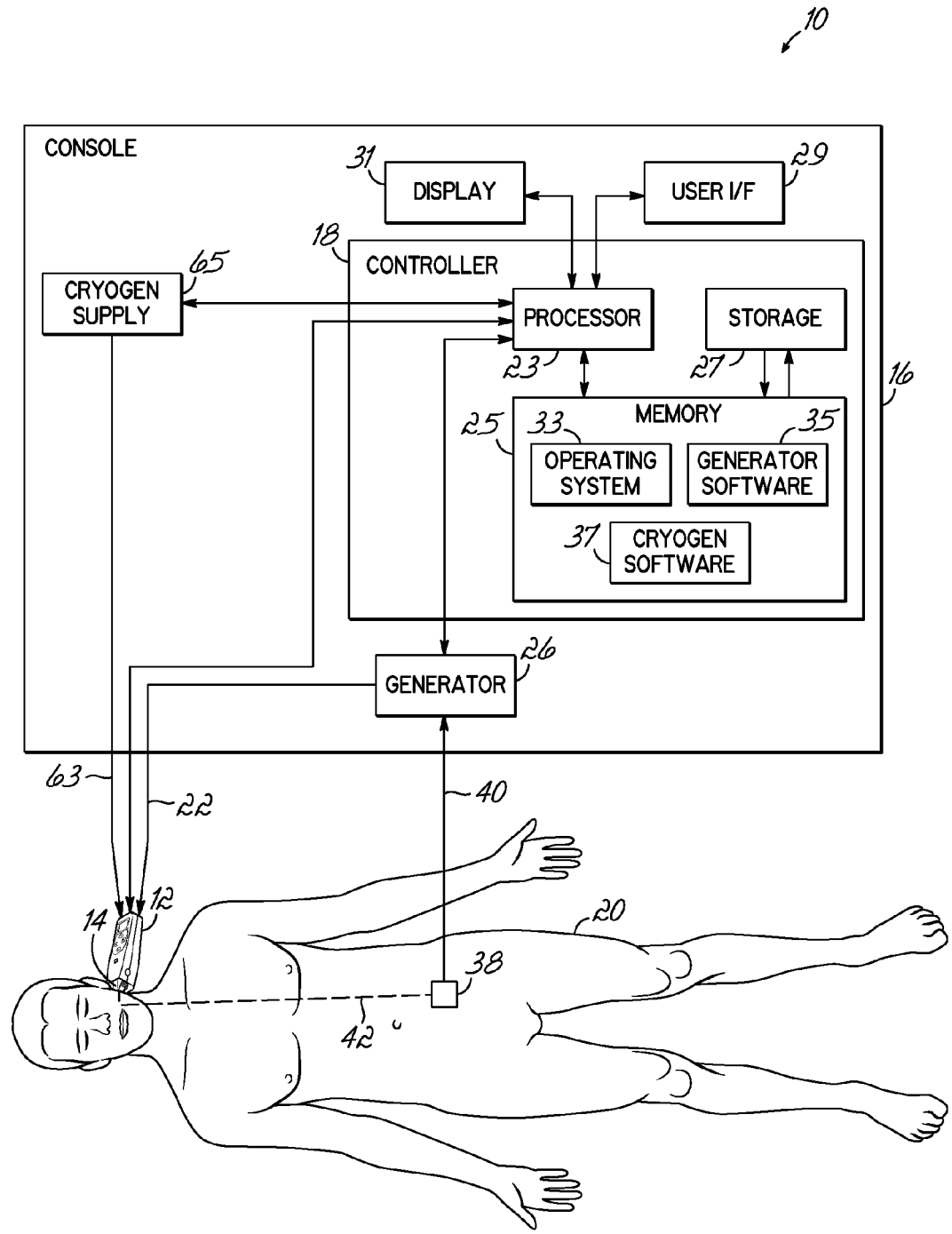
FIG. 1 is a diagrammatic view of a treatment system with a handpiece, a treatment tip, a console, and a generator in accordance with an embodiment of the invention.
Figure 2:
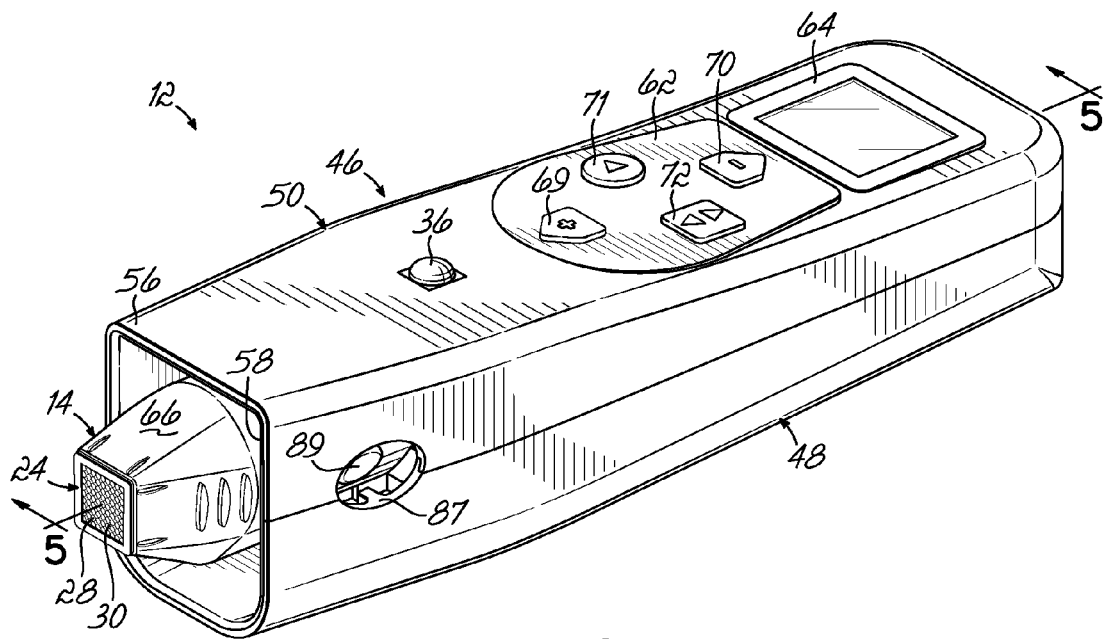
FIG. 2 is a perspective view of an assembly consisting of an embodiment of the handpiece and treatment tip for use with the treatment system of FIG. 1.
Figure 3:
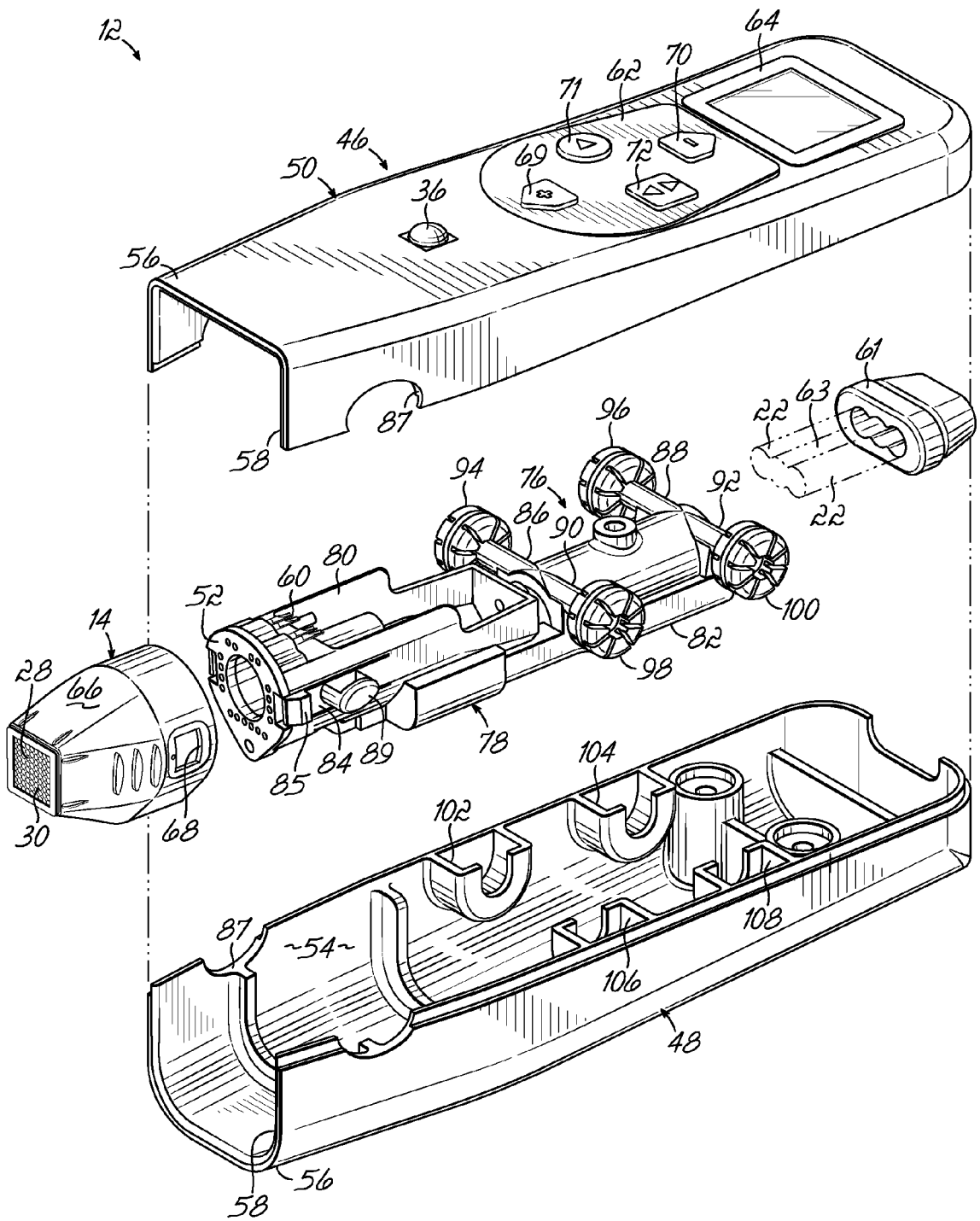
FIG. 3 is an exploded view of the assembly of FIG. 2.
Figure 9:
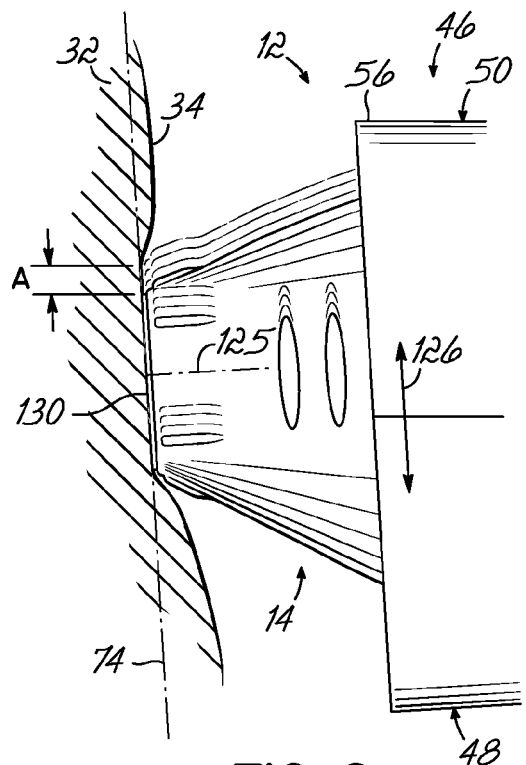
FIG. 9 is a detailed view of the treatment tip and a forward end of the handpiece in use during a treatment procedure conducted using the treatment system of FIGS. 1-8.
Figure 15:
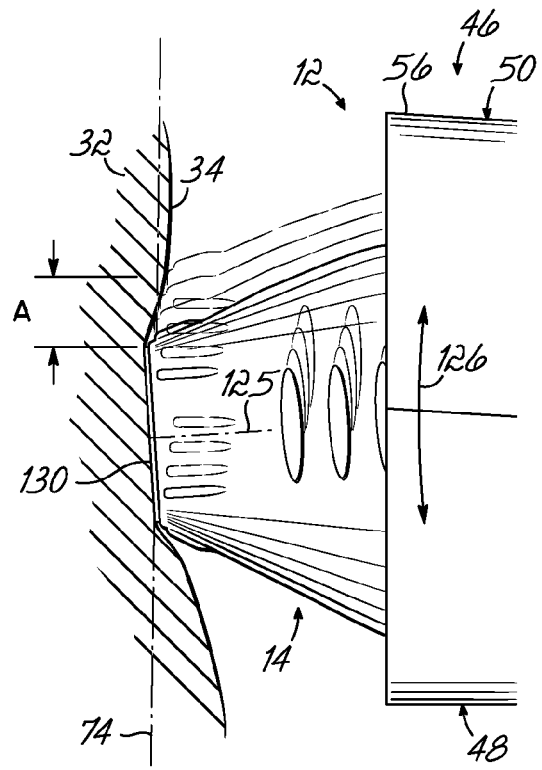
FIG. 15 is a detailed view similar to FIG. 9 of the treatment tip in use during a treatment procedure conducted using the treatment system of FIGS. 1 and 10-14.
Figure 10:
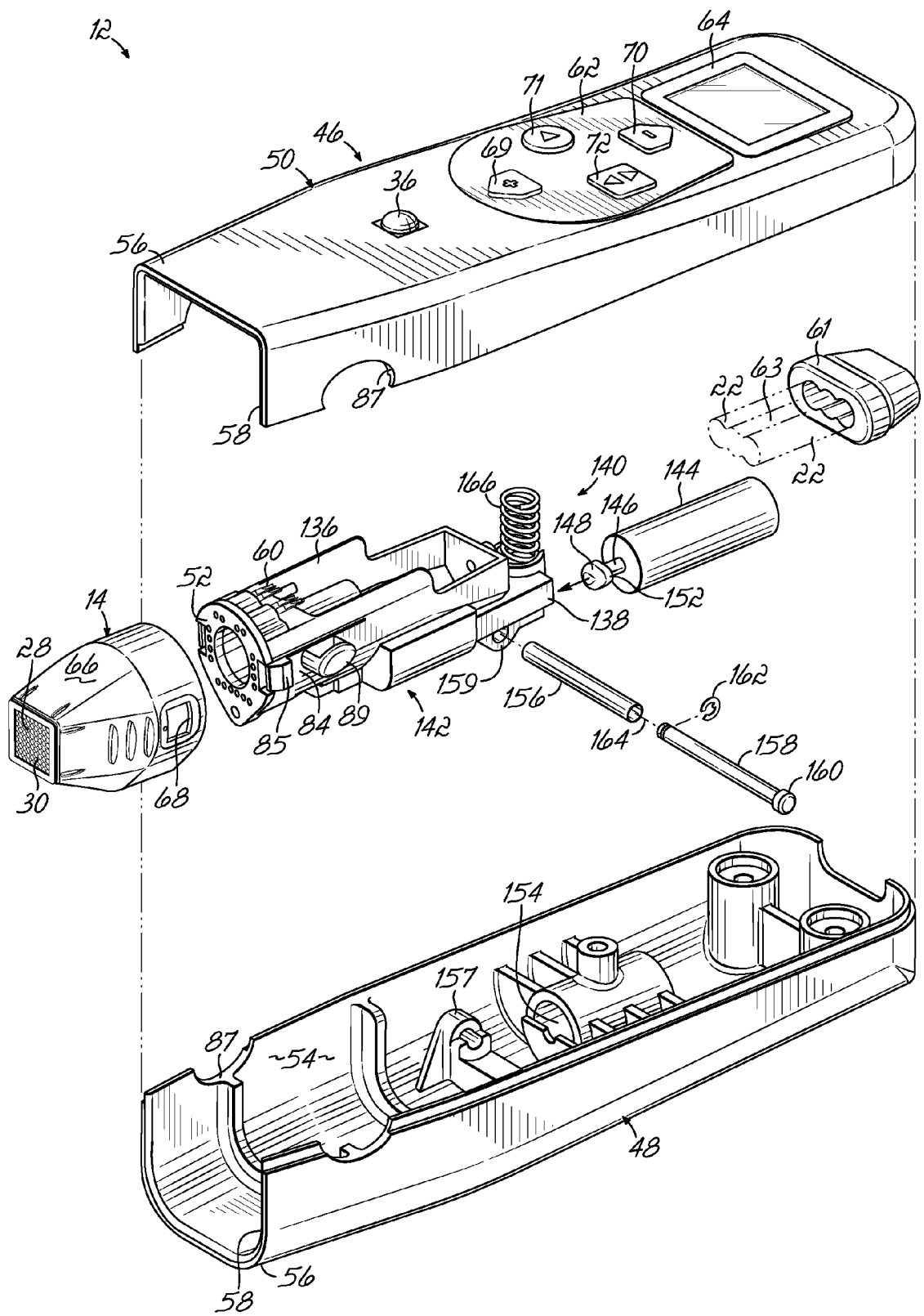
FIG. 10 is an exploded view of a handpiece and treatment tip assembly that includes a vibration device in accordance with an alternative embodiment of the invention.
Figure 11:
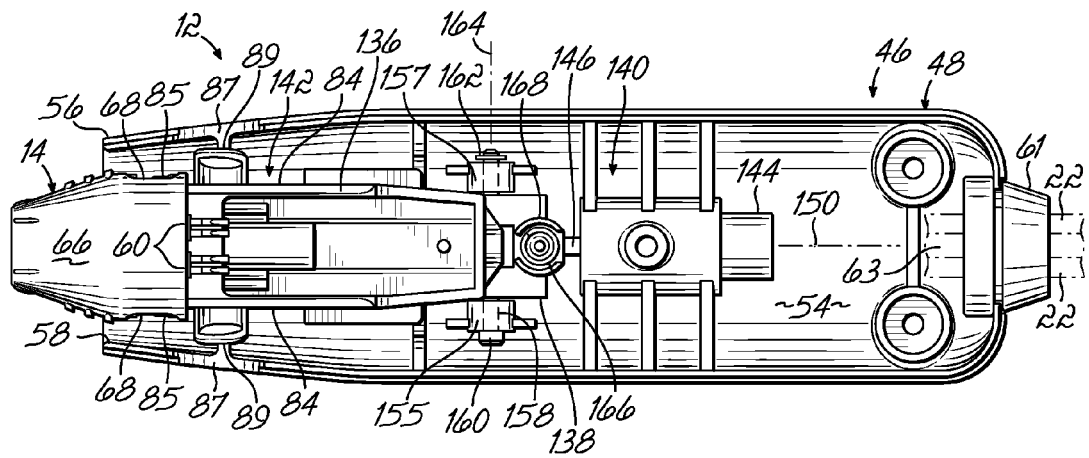
FIG. 11 is a top view of the assembled handpiece and treatment tip of FIG. 10 with the cover of the handpiece removed to expose the interior of the handpiece and the vibration device.

With reference to FIGS. 1-3, a treatment apparatus 10 generally includes a handpiece 12, a treatment tip 14 coupled in a removable and releasable manner with the handpiece 12, a console generally indicated by reference numeral 16, and a system controller 18. The system controller 18, which is incorporated into the console 16, orchestrates the global operation of the different individual components of the treatment apparatus 10. Under the control of the system controller 18 and any operator interaction with the system controller 18 at the console 16 and with controls at the handpiece 12, the treatment apparatus 10 is adapted to non-invasively and non-ablatively deliver electromagnetic energy in a high frequency band of the electromagnetic spectrum to a region of a patient's tissue 32 (FIG. 9). The delivered electromagnetic energy heats the tissue 32 to a targeted temperature range. The elevation in temperature will produce for example, changes in collagen fibers that achieve a desired treatment result, such as removing or reducing wrinkles and otherwise tightening the skin to thereby improve the appearance of a patient 20 receiving the treatment.

The treatment tip 14 carries an electromagnetic energy delivery member in the representative form of an active treatment electrode 24. In a representative embodiment, the treatment electrode 24 may include an electrically-insulating substrate 30 composed of a non-conductive dielectric material and a region 28 of an electrical conductor carried on the electrically-insulating substrate 30. The conductor region 28 of the treatment electrode 24 is physically carried on a non-contact side of the substrate 30 and is therefore separated by the substrate 30 from a skin surface 34 (FIG. 9). In one embodiment, the substrate 30 of the treatment electrode 24 may comprise a thin flexible base polymer film carrying the conductor region 28 and thin conductive (e.g., copper) traces or leads on the substrate 30 that electrically couple the conductor region 28 with contact pads inside the treatment tip 14. The base polymer film of substrate 30 may be, for example, polyimide or another material with a relatively high electrical resistivity and a relatively high thermal conductivity. The conductive leads may contain copper or another material characterized by a relatively high electrical conductivity. Instead of the representative single conductor region 28, the conductor region 28 of treatment electrode 24 may be segmented into plural individual electrodes that can be individually powered to sequentially deliver electromagnetic energy to the tissue 32.

The conductor region 28 of the treatment electrode 24 is electrically coupled by a set of insulated and shielded conductors 22 that extend exteriorly of the handpiece 12 to the generator 26 at the console 16. The generator 26 is configured to generate the electromagnetic energy used in the treatment to impart a therapeutic effect by heating target tissue 32 beneath the patient's skin surface 34. The generator 26, which has the form of a high frequency power supply, is equipped with an electrical circuit operative to generate high frequency electrical current, typically in the radio-frequency (RF) band of the electromagnetic spectrum. The operating frequency of generator 26 may be in the range of several hundred kHz to about twenty (20) MHz. In one embodiment, the generator 26 is a 400 watt, 6.78 MHz high frequency generator. The electrical circuit in the generator 26 converts a line alternating current voltage into drive signals for the treatment electrode 24. The drive signals have an energy content and a duty cycle appropriate for the amount of power and the mode of operation that have been selected by the clinician, as understood by a person having ordinary skill in the art. In alternative embodiments, the treatment apparatus 10 may be configured to deliver energy in the infrared band, microwave band, or another high frequency band of the electromagnetic spectrum, rather than within the RF band, to the patient's tissue 32.

The system controller 18 may represent practically any computer, computer system, or programmable device recognized by a person having ordinary skill in the art and capable of carrying out the functions described herein, as will be understood by those of ordinary skill in the art. System controller 18 typically includes at least one processor 23 coupled to a memory 25. Processor 23 may represent one or more processors (e.g., microprocessors), and memory 25 may represent the random access memory (RAM) devices comprising the main storage of system controller 18, as well as any supplemental levels of memory, e.g., cache memories, non-volatile or backup memories (e.g. programmable or flash memories), read-only memories, etc. In addition, memory 25 may be considered to include memory storage physically located elsewhere in system controller 18, e.g., any cache memory in a processor 23, as well as any storage capacity used as a virtual memory, e.g., as stored on a mass storage device 27 or another computer (not shown) coupled to system controller 18 via a network.

System controller 18 also typically receives a number of inputs and outputs for communicating information externally. For interface with a user or operator, system controller 18 typically includes one or more user input devices (e.g., a keyboard, a mouse, a trackball, a joystick, a touchpad, a keypad, a stylus, and/or a microphone, among others) in the form of a user interface 29. The user interface 29 may be used to deliver instructions to the system controller 18 to adjust the generator 26 and to establish an arbitrary treatment setting based upon operator input at the handpiece 12. System controller 18 may also include a display 31 (e.g., a CRT monitor or an LCD display panel, among others).

System controller 18 operates under the control of an operating system 33, and executes or otherwise relies upon various computer software applications, components, programs, objects, modules, data structures, etc. In general, the routines executed by the system controller 18 to operate the treatment system 10, whether implemented as part of an operating system or a specific application, component, program, object, module or sequence of instructions will be referred to herein as "computer program code". The computer program code typically comprises one or more instructions that are resident at various times in various memory and storage devices in a computer, and that, when read and executed by one or more processors in a computer, causes that computer to perform the steps necessary to execute steps or elements embodying the various aspects of the invention.

Figure 17:
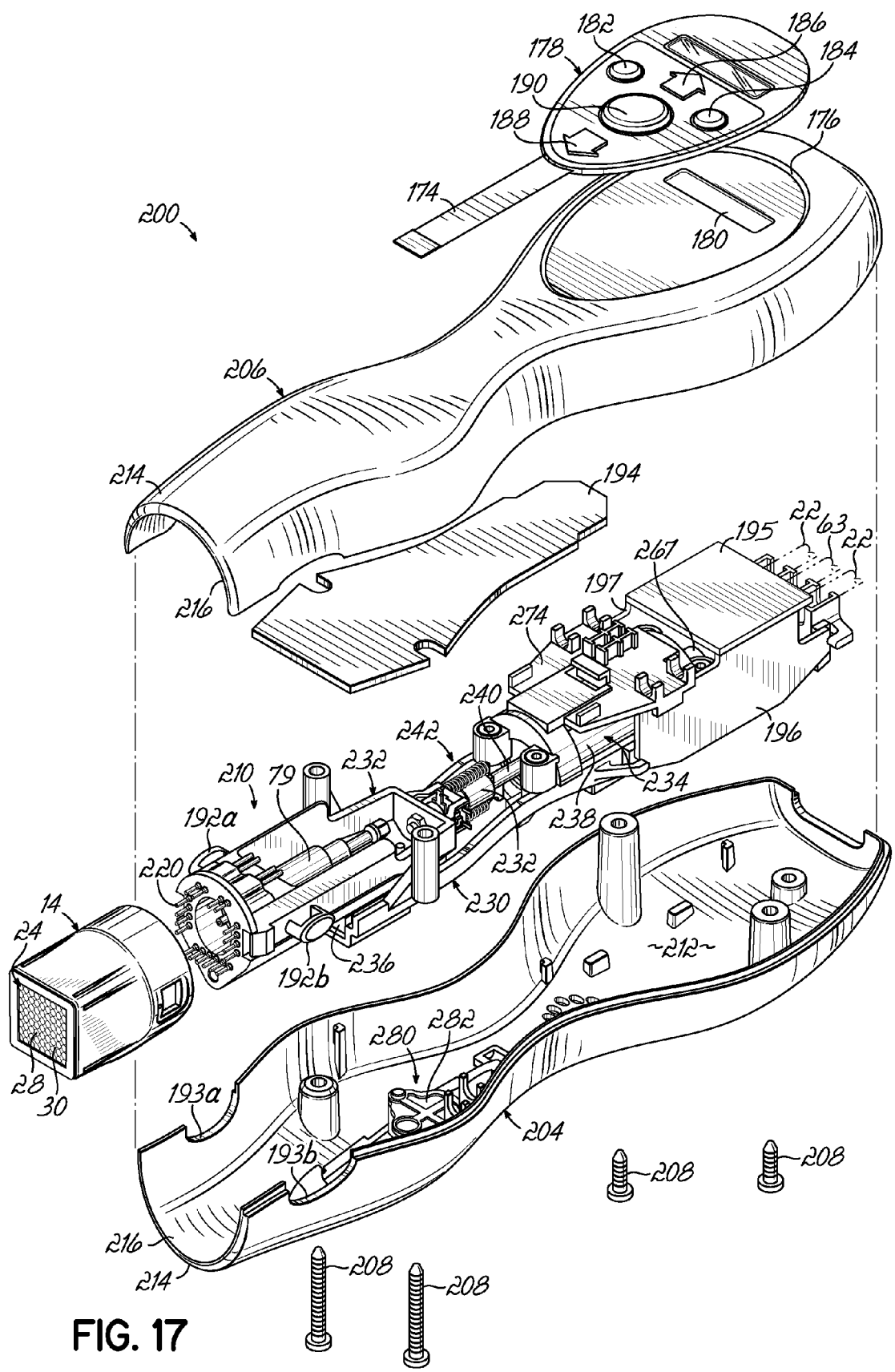
FIG. 17 is an exploded view of the assembly of FIG. 16.

The system controller 18 includes digital and/or analog circuitry that interfaces the processor 23 with the generator 26 for regulating the power delivered from the generator 26 to the treatment electrode 20. Generator software 35 resides as an application in the memory 25 and is executed by the processor 23 in order to issue commands that control the operation of the generator 26. The system controller 18 includes digital and/or analog circuitry that interfaces the processor 23 with a cryogen supply 65, such as a pre-filled canister containing pressurized cryogen, and a control valve 79 (FIG. 17) for regulating the cryogen delivered to the treatment electrode 20. Cryogen software 37 resides as an application in the memory 25 and is executed by the processor 23 in order to issue commands that control the operation of the cryogen supply 65 and the control valve 79.

During a non-ablative and non-invasive tissue treatment, a portion 130 (FIG. 9) of the treatment electrode 24 has a directly contacting relationship with the skin surface 34 of the patient 20. In the representative arrangement, the substrate 30 is arranged between the conductor region 28 and the skin surface 34 so that a portion of the substrate 30 directly contacts the skin surface 34. Electromagnetic energy is transmitted in a transcutaneous manner from the conductor region 28 through the thickness of substrate 30 and across the surface area of the portion 130 to the tissue 32 by capacitively coupling with the tissue 32 of the patient 20.

The treatment tip 14 includes temperature sensors (not shown), such as thermistors or thermocouples, that are constructed to detect the temperature of the treatment electrode 24 and/or treatment tip 14. The measured temperature reflects the temperature of the treated tissue 32 and may be used as feedback in a control loop controlling energy delivery and/or cooling of the skin surface. The handpiece 12 or treatment tip 14 may also include pressure sensors (not shown) for detecting physical contact between the treatment electrode 24 and the skin surface 34 of the patient 20.

An activation button 36, which is accessible to the operator from the exterior of the handpiece 12, is configured to be actuated to close a switch in a normally open circuit with the generator 26. The closed circuit energizes the treatment electrode 24. Actuation of the activation button 36 triggers delivery of the high frequency energy over a short timed delivery cycle to the target tissue 32. After a fixed amount of time has elapsed, the delivery of high frequency energy from the treatment electrode 24 to the tissue 32 at the treatment site is discontinued. The handpiece 12 is manipulated to position the treatment tip 14 near a different treatment site on the skin surface 34 and another cycle of high frequency energy is delivered to the patient's tissue 32. This process is repeated for an arbitrary number of treatment sites.

High frequency electrical current flowing between the treatment electrode 24 and the patient 20 is concentrated at the skin surface 34 and the underlying tissue 32 across the contacting surface area of the portion 130 of the treatment electrode 24. Capacitive coupling of the high frequency electromagnetic energy relies on energy transfer from the conductor region 28 through the dielectric material of the substrate 30 to create an electric field across the surface area where the treatment electrode 24 contacts the patient's body. The time-varying electric field induces electrical currents within the surrounding tissue 32 beneath the skin surface 34.

Because of the natural resistance of tissue 32 to electrical current flow, volumetric heating results within the tissue 32. The volumetric heating delivers a therapeutic effect to the tissue 32 near the treatment site. For example, heating to a temperature of 50° C. or 60° C. or higher will contract collagen, which will result in tissue tightening or another aesthetic effect to improve the patient's appearance. The heating depth in the tissue 32 is based upon the size and geometry of the treatment electrode 24 and, contingent upon the selection and configuration of the treatment tip 14, can be controlled to extend from a few hundred microns beneath the skin surface 34 to several millimeters.

A non-therapeutic passive return electrode 38 is used to electrically couple the patient 20 with the generator 26. During patient treatment, the high frequency current flows from the treatment electrode 24 through the treated tissue 32 and the intervening bulk of the patient 20 to the return electrode 38 and then to the generator 26 through conductors inside a return cable 40 to define a closed circuit or current path 42. The return electrode 38 is physically attached by, for example, an adhesive bond to a site on the body surface of the patient 20, such as the patient's back.

The surface area of the return electrode 38 in contact with the patient 20 is relatively large in comparison with the surface area of the treatment electrode 24. Consequently, at the tissue adjacent to the return electrode 38, the current density flowing from the patient 20 to the return electrode 38 is relatively low in comparison with the current density flowing from the treatment electrode 24 to the patient 20. Because negligible heating is produced at its attachment site to the patient, a non-therapeutic effect is created in the tissue adjacent to the return electrode 38.

Although the treatment electrode 24 and the return electrode 38 are representatively configured for the delivery of monopolar high frequency energy, the treatment electrode 24 may be configured to deliver bipolar high frequency energy. The modifications to the treatment apparatus 10 required to deliver bipolar high frequency energy are familiar to a person having ordinary skill in the art. For example, the return electrode 56 may be eliminated from the treatment apparatus 10 and a bipolar type of treatment electrode substituted for the monopolar treatment electrode 24.

With reference to FIGS. 2-5, the handpiece 12 is constructed from a housing 46 that includes a body 48, a cover 50 assembled by conventional fasteners with the body 48, and an electrical/fluid interface 52 for the treatment tip 14. The housing 46 may be fabricated by an injection molding process using a suitable polymer resin as a construction material. The body 48 and cover 50 constitute shell halves that are integrally fastened together as an assembly. The housing 46 encloses an interior cavity 54 bounded on one side by an interior surface of the body 48 and bounded on the other side by an interior surface of the cover 50. After the body 48 and cover 50 are assembled, the handpiece 12 has a smoothly contoured shape suitable for gripping and manipulation by an operator. The operator maneuvers the treatment tip 14 and treatment electrode 24 to a location proximate to the skin surface 34 and, typically, to place the treatment electrode 24 in a contacting relationship with the skin surface 34.

The housing 46 includes a nose 56 and a window 58 in the nose 56 that is sized for the insertion and removal of the treatment tip 14. The electrical/fluid interface 52 is disposed between the window 58 and the interior cavity 54 enclosed inside the housing 46. The treatment tip 14 is sized to be inserted through the window 58 and configured to be physically engaged with the handpiece 12, as described below. In the engaged state, the contact pads carried on the substrate 30 of the treatment electrode 24 establish respective electrical contacts with complementary electrical contacts 60 (FIG. 4), such as pogo pins, carried by the electrical/fluid interface 52 of the handpiece 12. These electrical contacts 60 are electrically coupled with one or more of the conductors 22 that extend from the handpiece 12 to the generator 26 and system controller 18. A portion of the treatment electrode 24 projecting outwardly from the nose 56 includes the portion 130 of the substrate 30 overlying the conductor region 28 so that the treatment electrode 24 is at least partially exposed through the window 58.

The handpiece 12 includes a control panel 62 and a display 64 that are carried by the cover 50. The control panel 62 may include various controls, such as controls 69, 70 used to respectively increase and reduce the treatment setting and controls 71, 72 that respectively enable and disable the controls 69, 70. The display 64 may be used to display information including, but not limited to, energy delivered, tissue impedance, duration, and feedback on procedure technique. The availability of the information displayed on the display 64 may conveniently eliminate the need to display identical information at the console 16 or may duplicate information displayed at the console 16. By displaying information at the handpiece 12, the operator can focus on the procedure without diverting his attention to glance at information displayed by the display on the console 16. In one embodiment, the display 64 may constitute a thin, flat liquid crystal display (LCD) comprised of a light source or reflector and an arbitrary number of color or monochrome pixels arrayed in front of the light source or reflector. A driver circuit (not shown) is provided to control the operation of the display 64.

The treatment tip 14 includes a rigid outer shell 66 and openings 68 defined on diametrically opposite sides of the outer shell 66. The openings 68 are used to temporarily secure the treatment tip 14 with the handpiece 12 in advance of a patient treatment procedure. The handpiece 12 is configured with a control valve 79 (FIG. 17) used to deliver a cryogen spray to the treatment electrode 24 for controlling the temperature of the treatment electrode 24. A conduit 63 extends through the interior cavity 54 inside the housing 46 and through a strain relief 61 held in an opening of the housing 46 of handpiece 12. The conduit 63 connects the control valve 79 with a cryogen supply 65, such as a pre-filled canister containing pressurized cryogen, stored at the console 16.

One purpose of the cryogen spray is to pre-cool the patient's epidermis, before powering the treatment electrode 24, by heat transfer between the treatment electrode 24 and the skin surface 34. The cooling creates a reverse thermal gradient in the tissue 32 such that the temperature of the tissue 32 at and near the skin surface 34 is cooler than the temperature of the tissue 32 deeper within the epidermis or dermis. As a result, the high frequency energy delivered to the tissue 32 fails to heat all or a portion of the patient's epidermis to a temperature sufficient to cause significant epidermal thermal damage. Depths of tissue 32 that are not significantly cooled by pre-cooling will warm up to therapeutic temperatures, which cause a desired therapeutic effect. The amount and/or duration of pre-cooling may be used to select the protected depth of untreated tissue 32. The cryogen delivered by the control valve 79 (FIG. 17) may also be used to cool portions of the tissue 32 during and/or after heating by the high frequency energy transferred from the treatment electrode 24. Post-cooling may prevent or reduce heat delivered deeper into the tissue 32 from conducting upward and heating shallower tissue regions, such as the epidermis, to temperatures which could thermally damage shallower tissue regions even though external energy delivery to the targeted tissue 32 has ceased.

Various duty cycles of cooling and heating that rely on cooling and high frequency energy transfer from the treatment electrode 24 are utilized contingent upon the type of treatment and the desired type of therapeutic effect. The cooling and heating duty cycles may be controlled and coordinated by operation of the controller 18. Suitable cryogens include low boiling point fluids, but are not limited to, R134a (1,1,1,2-Tetrafluoroethane) refrigerant, liquid nitrogen, and R152a refrigerant (1,1-Difluoroethane). Heat can be extracted from the treatment electrode 24 by virtue of evaporative cooling of the low boiling point fluid, which cools the treatment electrode 24. In alternative embodiments, the patient's skin and/or the treatment electrode 24 may be cooled in a different manner, such as with a thermoelectric or Peltier device, closed-loop fluid cooling, or a Zimmer cooler that is configured to deliver a forced stream of cold air onto the skin surface 34.

Figure 4:
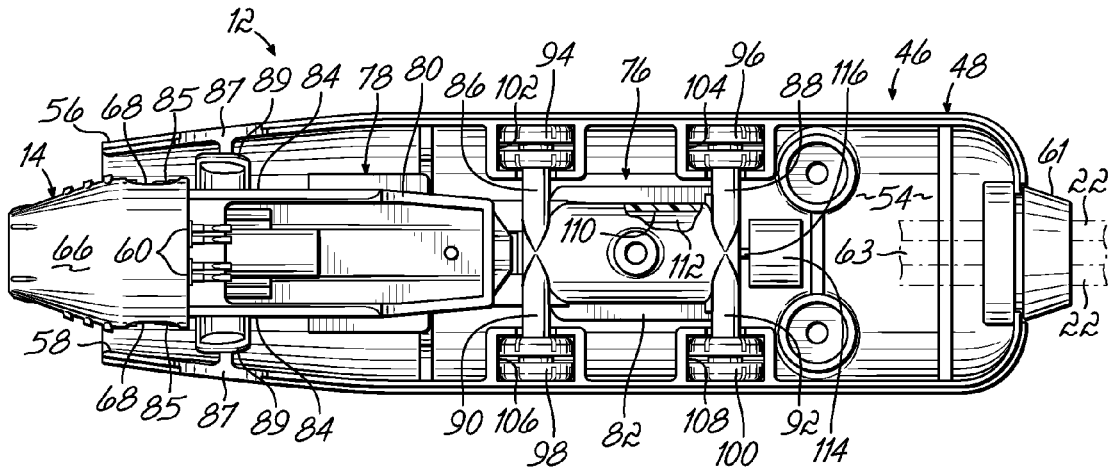
FIG. 4 is a top view of the assembly of FIG. 2 with the cover of the handpiece removed to expose the interior of the handpiece and a vibration device in accordance with an embodiment of the invention.
Figure 5:
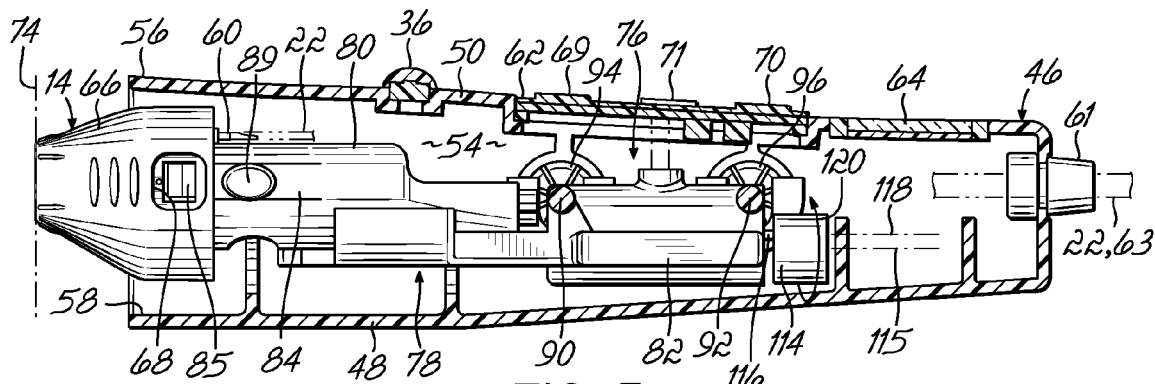
FIG. 5 is a side cross-sectional view of the handpiece taken generally along line 5-5 in FIG. 2.
Figure 6:
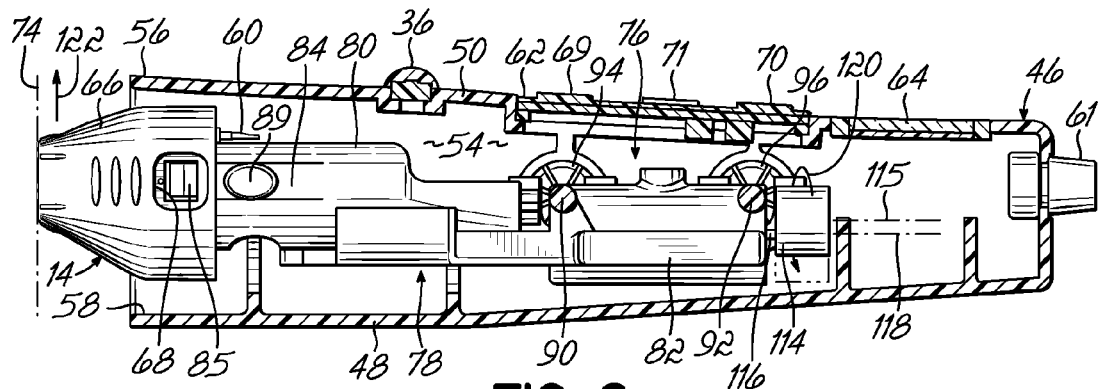
FIGS. 6-8 are side cross-sectional views similar to FIG. 5 illustrating the operation of the treatment system to use the vibration device to move the treatment tip relative to the skin surface of the patient.

With reference to FIGS. 3-5, the handpiece 12 of the treatment apparatus 10 incorporates a vibrator or vibration device, generally indicated by reference numeral 76. The vibration device 76 is configured to oscillate or vibrate the treatment tip 14 and treatment electrode 24 at a relatively low frequency relative to the headpiece 12 and the skin surface 34. In particular, the vibration device 76 causes the portion of the substrate 30 of the treatment electrode 24 in direct contact with the skin surface 34 to oscillate or vibrate laterally within a plane 74 that is substantially parallel to the skin surface 34. The plane 74 reflects the planar nature of the portion of the skin surface 34 that contacts the treatment electrode 24 during a treatment procedure.

The vibration device 76 includes a carriage 78 located within the interior cavity 54 of housing 46. The carriage 78 supports the electrical/fluid interface 52 that is coupled with the treatment tip 14. The carriage 78 is comprised of a first carriage member 80 and a second carriage member 82 rigidly joined with the first carriage member 80 to define an integral structure. In an alternative embodiment, the carriage 78 may be a unitary structure that combines the first and second carriage members 80, 82 to form a construction consisting of a single piece of material.

Spring arms 84 are located on opposite sides of the carriage 78 and each of the spring arms 84 includes an outwardly-projecting tab 85. When the treatment tip 14 is mounted to the handpiece 12, the spring arms 84 deflect inwardly when contacted by a portion of the outer shell 66 of the treatment tip 14. As the inward motion of the treatment tip 14 toward the electrical/fluid interface 52 continues, each of the tabs 85 eventually become registered with one of the openings 68. This registration permits the spring arms 84 to resiliently cantilever outwardly so that the tabs 85 engage the openings 68. The treatment tip 14 is released for removal from the handpiece 12 by manually applying inward pressure through access ports 87 in the housing 46 to buttons 89 on the spring tabs 84. The inward pressure disengages the tabs 85 from the openings 68, which releases the engagement between the handpiece 12 and treatment tip 14 and permits the treatment tip 14 to be separated from the handpiece 12. After separation from the handpiece 12, the treatment tip 14 may be discarded or may be retained for a future treatment procedure.

Projecting outwardly from one side of the carriage 78 are arms 86, 88 and projecting outwardly from an opposite side of the carriage 78 are arms 90, 92. One of a plurality of vibration dampers 94, 96, 98, 100 is attached to the free end of each of the arms 86, 88, 90, 92. The vibration dampers 94, 96, 98, 100 are received in recesses 102, 104, 106, 108 partially defined in the body 48 of the housing 46 of the handpiece 12 and partially defined in the cover 50 of the housing 46. When the body 48 and cover 50 are assembled together, the vibration dampers 94, 96, 98, 100 are captured within the recesses 102, 104, 106, 108 to supply a mechanical connection between the housing 46 and the vibration device 76 and operate to suspend the carriage 78 relative to the housing 46 of the handpiece 12. The vibration dampers 94, 96, 98, 100 are formed from a relatively soft durometer elastomeric material, such as a silicone rubber, which contributes to the vibration isolation of the housing 46.

The carriage 78 includes an electric motor 112 and a cavity 110 that is shaped to receive the electric motor 112. For example, the cavity 110 and the outer casing of the electric motor 112 may each have the geometrical shape of a right circular cylinder. A fastener (not shown) may be used to physically connect the electric motor 144 with the carriage 78.

An off-center or eccentric counterweight 114 is attached to one end of an output shaft 116 of the electric motor 112. The counterweight 114 is spun by the electric motor 112 about an axis of rotation 118 that is generally collinear with the output shaft 116. The counterweight 114 has a center of mass 115 that is offset or spaced apart from the axis of rotation 118 of the output shaft 116. As a result, the center of mass 115 of the counterweight 114 and the axis of rotation 118 of the output shaft 116 are not collinear. When the electric motor 112 is energized and operating to spin the counterweight 114, the off-balance motion of the mass of the counterweight 114 induces a vibration in the electric motor 112, which is transferred from the electric motor 112 to the carriage 78 and, ultimately, from the carriage 78 to the treatment tip 14 and treatment electrode 24.

The vibration amplitude, A, and the vibration frequency may be adjusted to achieve a targeted reduction in the pain perceived by the patient 20. The vibration amplitude, A, represents the maximum displacement of the portion 130 of the treatment electrode 24 in contact with the skin surface 34 relative to a normal or neutral position (FIG. 5). The vibration amplitude, A, determines the range of transverse or lateral motion for the portion 130 of the treatment electrode 24 in contact with the skin surface 34 relative to the neutral position and, thereby, the surface area on the skin surface 34 effectively contacted by the substrate 30 of the treatment electrode 14 during each complete oscillation between the positive and negative amplitudes. For example, increasing the amplitude, A, increases the effective surface area on the skin surface 34 contacted by the treatment electrode 24 and will average the energy density transferred to the tissue 32 across the effective surface area so that the hot spot thermal zones near the peripheral edge of the treatment electrode 24 are reduced. The vibration frequency is determined from the time to complete a fully cycle for the vibration, such as measured from positive amplitude to the next positive amplitude or measured from the negative amplitude to the subsequent negative amplitude. The lateral or transverse motion of the portion 130 of the treatment electrode 24 in contact with the skin surface 34 is defined as a direction transverse to a surface normal 125 to the skin surface 34.

The treatment tip 14 may include a tip frame as described in U.S. Application No. 61/143,537, filed Jan. 9, 2009 and, and U.S. Application No. 61/226,138, filed Jul. 16, 2009, each entitled "Tissue Treatment Apparatus and Systems with Pain Mitigation and Methods for Mitigating Pain During Tissue Treatments", which are hereby incorporated by reference herein in their entirety. The tip frame may contact the skin surface 34 and space a peripheral portion of the treatment electrode 24 from the skin surface 34. A portion of the rigid outer shell 66 of the treatment tip 14 encircling the treatment electrode 24 may also be in a contacting relationship the skin surface 34. In each instance, the vibration may be transferred at least in part by a structural contact other than the portion 130 of the treatment electrode 24.

In one embodiment, the motor 112 may be a direct current (DC) motor that is controlled by a DC drive voltage supplied from a power supply (not shown) at the system controller 18 through at least one of the insulated and shielded conductors 22. The DC drive voltage energizes the motor windings and causes rotates the output shaft 116 and counterweight 114, preferably at a constant angular velocity, about the axis of rotation 118. The portion 130 of the treatment electrode 24 in contact with the skin surface 34 will cyclically move from the positive vibration amplitude to the negative vibration amplitude and then from the negative vibration amplitude to the positive vibration amplitude as the counterweight 114 rotates. The vibration amplitude, A, increases in magnitude proportionate to the magnitude of DC drive voltage used to control the motor 112. The strength of the vibrations is also directly linked to the vibration frequency, which is proportional to the angular velocity of the counterweight 114 about the axis of rotation 118. Increasing the angular velocity of the counterweight 114 by operating the motor 112 at a higher speed (higher frequency of motion) also operates to increase the vibration magnitude.

In an alternative embodiment, the DC drive voltage may control the motor 112 to bidirectionally rotate the counterweight 114 and output shaft 116 about the axis of rotation 118. The direction of rotation of the counterweight 114 about the axis of rotation 118 is alternated with an appropriate drive waveform for the DC drive voltage. The counterweight 114 travels through only a portion of a full revolution of the output shaft 116 before the counterweight 114 changes direction and moves in the opposite direction. This causes a vibration in the electric motor 112 and in the carriage 78 coupled to the electric motor 112 as the counterweight 114 is rapidly moved back and forth in a cyclic rocking motion relative to the axis of rotation 118.

The vibration amplitude, A, of the treatment tip 14 can also be increased or decreased, respectively, by increasing or decreasing the mass and/or geometrical shape of the counterweight 114. Because of the nature of the non-rigid mechanical connections, the vibration dampers 94, 96, 98, 100 operate to effectively enhance or amplify the vibration amplitude of the carriage 78. The vibration amplitude, A, can be also controlled by changing properties, such as size and durometer, of the vibration dampers 94, 96, 98, 100. The greatest magnitude for the vibration amplitude, A, may be output near a resonance frequency of the vibration device 76, which is determined by the mass of the counterweight 114 and by the compliance of the vibration dampers 94, 96, 98, 100.

In the representative embodiment, the counterweight 114 has a cylindrical shape. However, many different types and geometrical shapes of counterweight 114 can be used. For example, the counterweight 114 may be wedge- or pie-shaped eccentric with one end of the eccentric coupled to the output shaft 116 so that the majority of the mass extends to one side of the output shaft 116. The offset between the center of mass 115 of the counterweight 114 and the axis of rotation of the output shaft 114 can be adjusted in different device embodiments to provide stronger or weaker vibrations, as desired to achieve a particular pain management effect.

In various embodiments, the lateral vibration amplitude, A, may be on the order of several millimeters, typically 5 millimeters or less, and the vibration frequency may be on the order of 5 Hz to 1 kHz, preferably between in a range of 20 Hz to 100 Hz. The window 58 of the handpiece 12 is preferably dimensioned in relation to extent of the vibration amplitude, A, such that the outer shell 66 of the treatment tip 14 does not contact the housing 46 of the handpiece 14 when vibrated. The clearance ensures that the handpiece 14 does not interfere with the vibration of the treatment tip 14.

Because the mechanical connections between the carriage 78 and housing 46 of the handpiece 12 are not rigid, the vibration dampers 94, 96, 98, 100 operate to dampen the resonance between the carriage 78 and the housing 46 of the handpiece 12. In particular, this non-rigid mechanical connection reduces the vibration perceived by an operator grasping the housing 46 of the handpiece 12.

With reference to FIGS. 5-9, the use of the vibration device 76 is illustrated. The counterweight 114 is continuously spun by the electric motor 112, when motor 112 is energized, about the axis of rotation 118 in a direction generally indicated by the single-headed arrow 120. During one half of a complete revolution, the center of mass 115 of the counterweight 114 is located above the axis of rotation 118. While the center of mass 115 and the axis of rotation 118 have this spatial relationship, the carriage 78 and treatment tip 14 move in a direction indicated by the single-headed arrow 122 in FIG. 6 from the neutral position shown in FIG. 5. The resulting motion of the portion 130 of treatment electrode 24 contacting skin surface 34 is generally within the plane 74.

Figure 7:
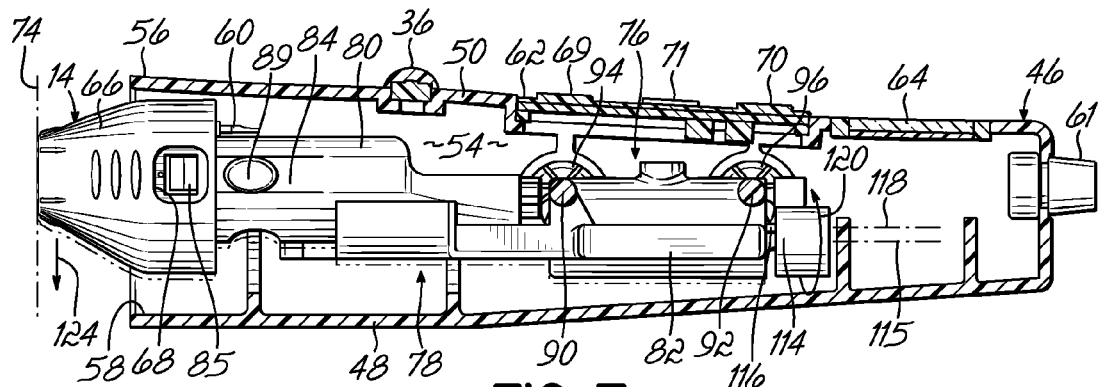
Figure 8:
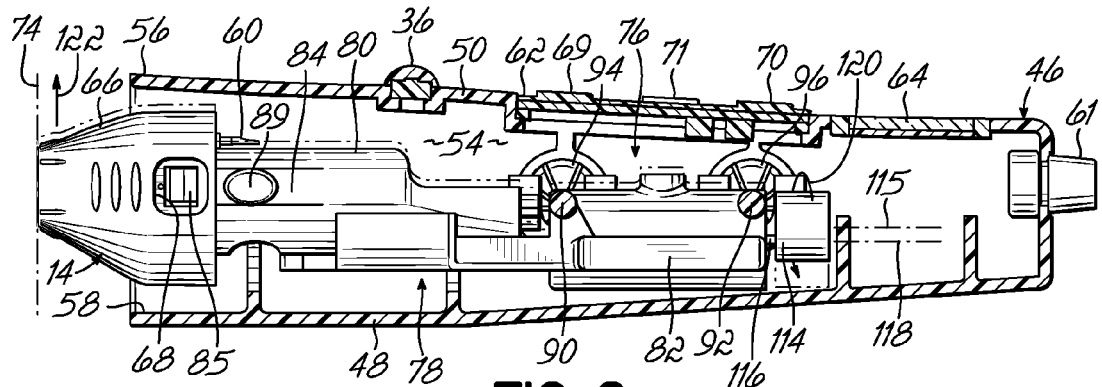

Immediately after the positive vibration amplitude is reached, as shown in FIG. 7, the treatment tip 14 and carriage 78 will reverse direction and move the treatment electrode 24 generally in a direction within plane 74 indicated by the single-headed arrow 124 in FIG. 7. During this half of a complete revolution of the counterweight 114, the center of mass 115 of the counterweight 114 is located below the axis of rotation 118. When the negative vibration amplitude is reached, as shown in FIG. 8, the treatment tip 14 and carriage 78 will reverse direction and again move the treatment electrode 24 generally in direction 122 within plane 74 toward the neutral position shown in FIG. 5 and eventually to the position of positive vibration amplitude in FIG. 7.

The motion of the treatment tip 14 and carriage 78 moves the portion 130 of the treatment electrode 24 in contact with the skin surface 34 transversely or laterally within plane 74 relative to the skin surface 34 and relative to the handpiece 12, as best shown in FIG. 9. In FIG. 9, the portion 130 of the treatment electrode 24 is shown as moving relative to the skin surface 34 through the positive amplitude, A, over one-half of its full range of motion. During the vibration, electromagnetic energy is transferred from the conductor region 28 through the portion 130 of the substrate 30 to the tissue 32. The oscillating or vibrational nature of the transverse motion laterally relative to the skin surface 34, which is indicated generally by the double headed arrow 126, operates to reduce the pain experienced by the patient during the treatment procedure. Contact between the portion 130 of the treatment electrode 24 and the skin surface 34 tends to slightly deform the tissue, as apparent in FIG. 9.

With reference to FIGS. 10-15 and in accordance with an alternative embodiment of the invention, a vibrator in the representative form of a vibration device 140 includes a carriage 142, an electric motor 144, a output shaft 146 coupled with the electric motor 144, and a cam element 148 mounted to one end of the output shaft 146. The output shaft 146 is rotated by the electric motor 144 about an axis of rotation 150 generally collinear with the output shaft 146. The carriage 142, which is located within the interior cavity 54 of housing 46, supports the electrical/fluid interface 52. The carriage 142 is comprised of a first carriage member 136 and a second carriage member 138 rigidly joined by conventional fasteners with the first carriage member 136 to define an integral structure. In an alternative embodiment, the carriage 142 may have a unitary construction that combines the first and second carriage members 136, 138 into a single piece of material.

The body 48 of the handpiece 12 includes a chamber 145 that is shaped to hold the electric motor 144. In one embodiment, the electric motor 144 may be a direct current (DC) motor that is energized by power supplied from the system controller 18 through at least one of the insulated and shielded conductors 22. A fastener (not shown) may be used to physically connect the electric motor 144 with the body 48 of the handpiece 12.

Figure 14:
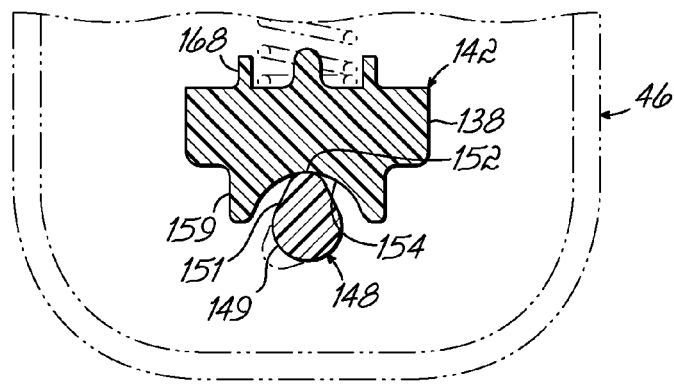
FIG. 14 is a cross-sectional view taken generally along line 14-14 in FIG. 12.

The cam element 148, which is rigidly affixed to the end of the output shaft 146, has a peripheral surface that is characterized by an eccentric shape with a circular section 149 and a non-circular section 151 that contact a curved cam surface 154 defined in the carriage 142. The non-circular section 151 features an off-center apex 152 that is offset laterally from the axis of rotation 150 of the output shaft 146. The shape of the cam element 148 is representatively pear shaped or teardrop shaped, although the embodiments of the invention are not so limited as the sections 149, 151, which are best shown in FIG. 14, may differ from the representative embodiment.

The cam element 148 translates circular or rotary motion of the output shaft 146 driven about the axis of rotation 150 by the electric motor 144, when energized, into oscillating or rocking motion of the carriage 142. Vibration or oscillation of the carriage 142 causes the treatment tip 14 and, in particular, the portion 130 of the treatment electrode 24 in contact with the skin surface 34 to likewise vibrate in the plane 74 and relative to the skin surface 34. Specifically, the cam element 148 produces a smooth reciprocating motion of the carriage 142 back and forth as the sections 149, 151 periodically ride in a track along the curved cam surface 154 defined in the carriage 142. In a representative embodiment, the cam surface 154 is a section of an arcuate surface, such as a cylinder, and, preferably, is approximately one-half of a right cylindrical section that provides a drive surface for the cam follower represented by the cam element 148. The vibration amplitude, A, of the treatment tip 14 can be increased or decreased by, for example, increasing or decreasing the profile of the cam element 148 so that the distance between the apex 152 and axis of rotation 150 is altered. The vibration frequency is increased or decreased by increasing or decreasing, respectively, the speed of the electric motor 144.

The carriage 142 is mechanically connected with the housing 46 by a bushing 156 and a shaft 158 received inside a bore extending centrally through the bushing 156. The bushing 156, which extends transversely across the width of the interior cavity 54, has opposite ends captured within bores defined in a spaced-apart pair of mounting flanges 155, 157 and a central portion that is captured within an opening in a mounting flange 159 integrally formed with the carriage 142. The mounting flanges 155, 157 are integrally formed with the body 48 and are spaced apart by a distance sufficient to prevent contact between the body 48 and the carriage 142. The openings in the mounting flanges 155, 157 are aligned with the opening in the mounting flange 159, and the mounting flanges 155, 157 are disposed on opposite sides of mounting flange 159 in the assembly. When the carriage 142 is connected with the housing 46, the carriage 142 is positioned between the electric motor 144 in chamber 145 and the electrical/fluid interface 52.

The shaft 158 has an enlarged head 160 at one end that is larger than the inner diameter of the bore in bushing 156 and an opposite end that projects from the bushing 156. The former end of the shaft 158 is secured with a fastener 162, such as a C-clip, that blocks any substantial transverse movement of the shaft 158 relative to the bore of the bushing 156 and the mounting flange 157. The enlarged head 160 and fastener 162 capture the shaft 158 and bushing 156 with the mounting flanges 155, 157 and limit the extent of lateral movement of the shaft 158 and bushing 156, as well as the extent of the lateral motion of the carriage 142. The shaft 158 freely rotates about a fixed pivot axis 164 generally aligned with the coincident centerlines of the shaft 158 and the bore of bushing 156, and generally aligned transverse to the axis of rotation 150 of the output shaft 146. The amplitude for the motion of the portion 130 of treatment electrode 24 is also related to the distance from the pivot axis 164. The carriage 142 is restrained against any linear movement relative to the housing 46.

A biasing element, which has the representative form of a compression spring 166, applies a continuous downward force on the carriage 142. The compression spring 166 is captured in a compressed state between a boss 168 on the carriage 142 and another boss 169 on the cover 50 of the housing 46. The bosses 168, 169 are sized to receive and secure the opposite ends of the compression spring 166. Alternatively, a different type of biasing element other than a compression spring 166 may be used to apply the continuous downward biasing force to the carriage 142. The continuous downward force applied by the compression spring 166 to the carriage 142 ensures that the cam surface 154 remains in constant contact with the sections 149, 151 of the cam element 148 and prevents wobbling or jittering of the carriage 142.

Figure 12:
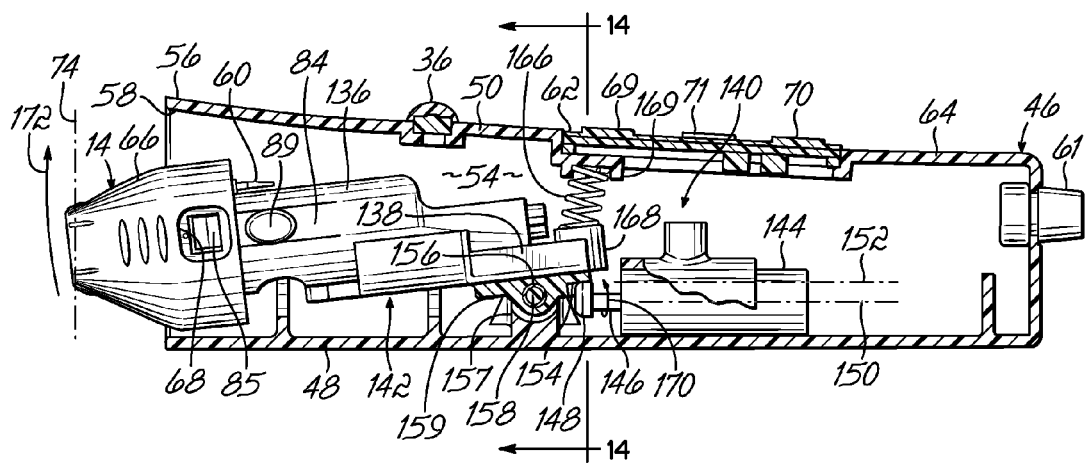
FIGS. 12 and 13 are side cross-sectional views illustrating the operation of the treatment system in which the vibration device of FIG. 11 is moving the treatment tip relative to the skin surface of the patient.

With reference to FIGS. 12-15, the operation of the vibration device 140 may be illustrated. When energized, the electric motor 144 rotates the output shaft 146 and the cam element 148 in a direction indicated by the single-headed arrow 170 and preferably at a constant angular velocity. For purposes of description, the carriage 142 may initially be in the position as shown in FIG. 12 at which the non-circular section 151 of the cam element 148 has a contacting relationship with the curved cam surface 154 of the carriage 142. As best shown in FIG. 14, the cam element 148 has an angular orientation in which the apex 152 contacts the cam surface 154 to provide the positive amplitude (maximum positive displacement) shown in FIG. 12.

As the output shaft 146 is rotated by the electric motor 144, the non-circular section 151 of the cam element 148 remains in contact with the curved cam surface 154 of the carriage 142. Although the expansion of the compression spring 166 is constrained by the contact between the cam surface 154 and the non-circular section 151 of the cam element 148, the coils of the compression spring 166 progressively expand as the cam element 148 rotates. The contact between the non-circular section 151 and the curved cam surface 154 and the progressive expansion of the compression spring 166 causes the carriage 142 to rotate about the pivot axis 164 in a direction indicated by the single headed arrow 172 (FIG. 12). The treatment tip 14 and the portion 130 of the treatment electrode 24 move from the position of positive vibration amplitude shown in FIG. 12 toward a neutral position. As rotation continues, the non-circular section 151 of the cam element 148 maintains the contacting relationship with the curved cam surface 154 over approximately one-quarter of a complete revolution of the cam element 148.

Figure 13:
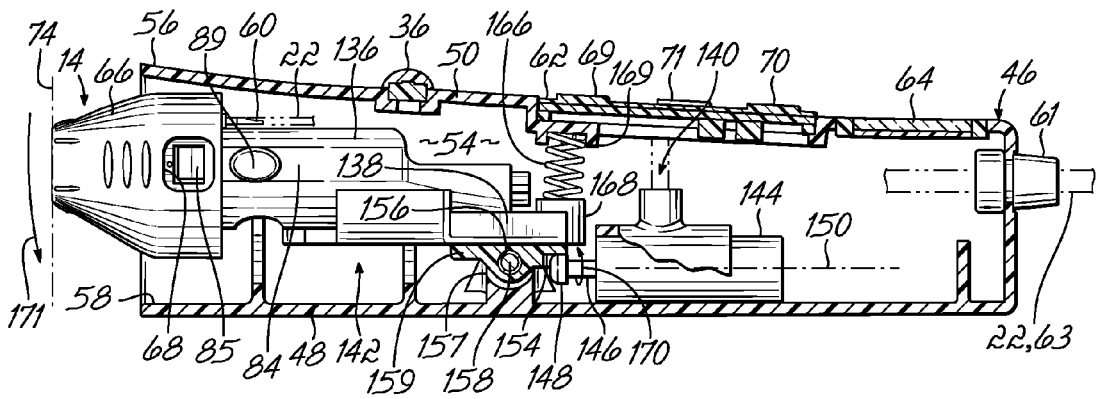
Figure 16:
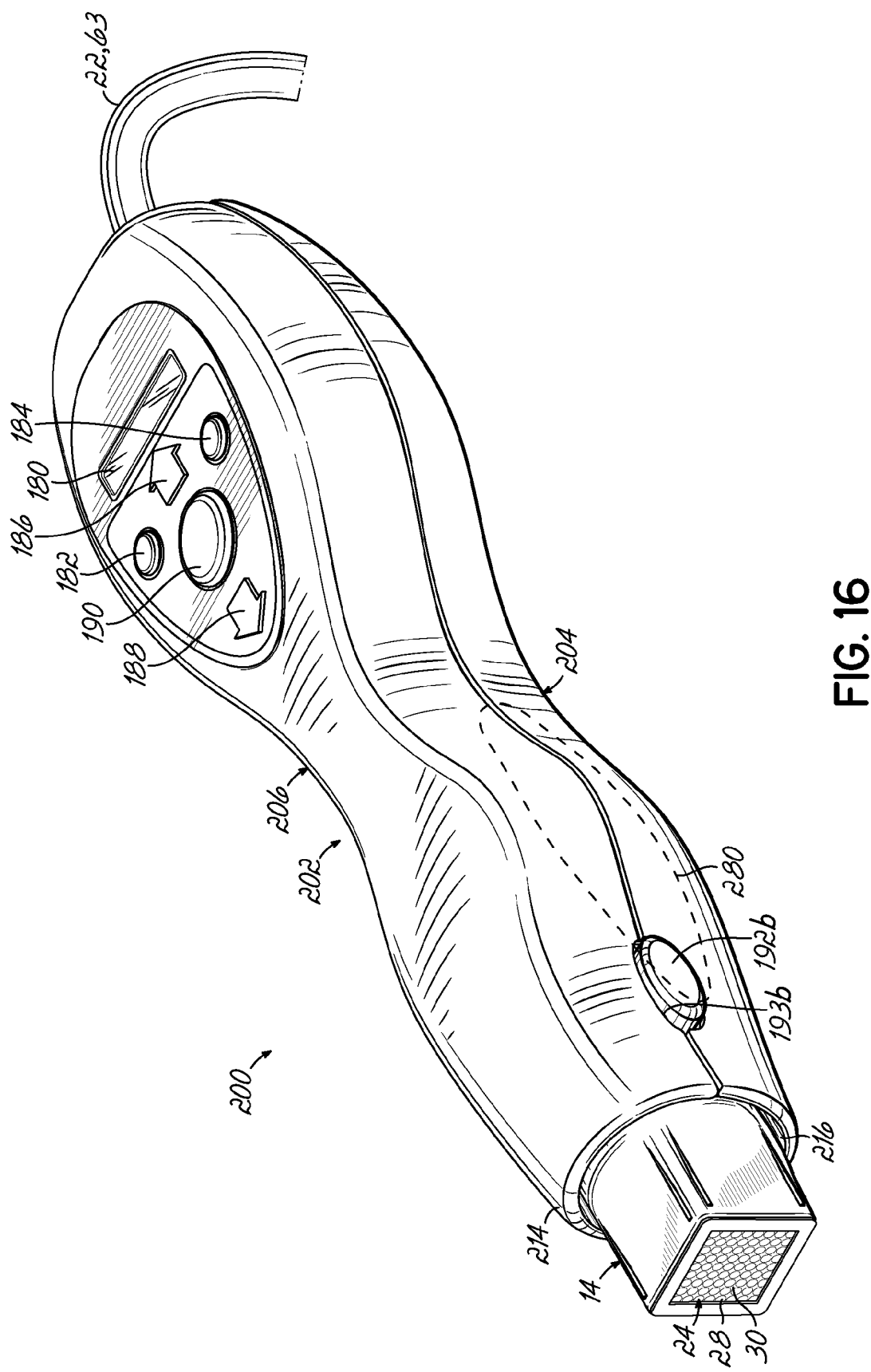
FIG. 16 is a perspective view of an assembly consisting of another alternative embodiment of the handpiece and treatment tip for use with the treatment system of FIG. 1.

Eventually, the cam element 148 assumes an angular orientation in which the non-circular section 151 has a non-contacting relationship with the curved cam surface 154 on the carriage 142, which represents a neutral position. The compression spring 166 continues to forcibly extend, unrestrained by the contact between the apex 152 and cam surface 154, and applies a spring force that urges the carriage 142 to continue to rotate about the pivot axis 164 in the direction 172, as shown in FIG. 12, toward the position of positive vibration amplitude for the portion 130 of the treatment electrode 24 shown in FIG. 13. The cam element 148 continues to rotate through angular orientations representing approximately one-half of a complete revolution. Eventually, the cam surface 154 and the circular portion 149 of the cam element 148 contact to halt the motion in the direction 172 with the portion 130 at the location of negative amplitude (maximum negative displacement), as shown in FIG. 13.

With advancing rotation, the non-circular section 151 of the cam element 148 again contacts the curved cam surface 154 on the carriage 142. This contacting relationship initiates movement of the carriage 142, treatment tip 12, and portion 130 of the treatment electrode 24 in a direction indicated by the single headed arrow 171 (FIG. 13). The non-circular section 151 of the cam element 148 maintains the contacting relationship with the curved cam surface 154 over approximately one-quarter of a complete revolution of the cam element 148, which moves the portion 130 of the treatment electrode 24 through the neutral position and toward the position with positive amplitude. The apex 152 ultimately reaches the angular orientation shown in FIG. 14 and the portion 130 of the treatment electrode 24 is again at the location of positive amplitude shown in FIG. 12. The cycle then repeats at the prescribed frequency of vibration. Thus, rotation of the cam element 148 causes the carriage 142, the treatment tip 14, and the portion 130 of the treatment electrode 24 to cyclically move approximately laterally or transversely relative to the skin surface 34.

In use to perform a treatment procedure, the physician selects a type of treatment tip 14 based on the procedure to be performed and the size of the surface area on the patient 20 to be treated, as well as the depth of cooling and heating desired for the treatment procedure. The procedure protocol may include a combination of pulse count, pulse duration, energy level, and heating profile. After choosing the treatment tip 14 and attaching it to the handpiece 12, the physician marks the intended treatment area on the patient 20 with a grid of removable markings that are easily wiped away post-procedure. Each discrete square in the grid corresponds approximately to the size of the portion 130 of the treatment electrode 24 that is placed in direct contact with the skin surface 34. The markings operate as a placement guide on the patient's skin surface 34 for the treatment procedure. The return electrode 38 is attached to the patient 20 to supply the current path 42 for the high frequency current back to the generator 26.

After the optional application of a conductive fluid, each square within the grid is sequentially treated with high frequency energy delivered from the treatment electrode 24. Specifically, at each grid square, the physician lands the portion 130 of treatment electrode 24 directly against the patient's skin and actuates the activation button 36 on the handpiece 12. The handpiece 12 processes information from the treatment tip 14 about skin temperature and contact, treatment force or pressure against the skin, cooling system function, and other types of relevant data. This information is sent from the handpiece 12 to the console 16 in order to generate the proper high frequency signal at the generator 26.

The control valve 79 (FIG. 17) regulates the delivery of cryogen, which cools and protects the skin's superficial layers proximate to the skin surface 34. The cryogen is used to pre-cool the patient's epidermis, before powering the treatment electrode 24, by extracting heat from the warmer skin The treatment electrode 24 transmits high frequency energy to the skin while serving as a contact cooling membrane for the cryogen. The controller 18 monitors a combination of inputs, such as temperatures, power levels and delivery duration, to precisely and safely control the high frequency energy and cooling delivery to each treatment site in the grid. Cooling the epidermis limits the temperature to lessen the likelihood of thermal damage to the epidermis. Depths of tissue 32 that are not significantly cooled by pre-cooling will be heated to therapeutic temperatures resulting in the desired therapeutic effect. The amount or duration of pre-cooling may be used to select the protected depth of untreated tissue 32.

The cryogen may also be used to cool the contacted tissue 32 during, before, and/or after heating by the transferred high frequency electromagnetic energy. Various duty cycles of cooling and heating by high frequency energy transfer are utilized depending on the type of treatment and the desired type of therapeutic effect. The cooling and heating duty cycles may be controlled and coordinated by operation of the system controller 18.

After energy delivery is completed, the handpiece 12 is maneuvered to lift the portion 130 of the treatment electrode 24 from the skin surface 34. The handpiece 12 and treatment tip 14 are moved among subsequent treatment locations in the grid and energy is delivered is a similar manner for treating large regions on the patient 20, such as the patient's face. Multiple passes over the entire grid of the treatment zone, separated in time by a quiescent period of few minutes, may be used to enhance the treatment, as is understood by persons skilled in the art. Multiple treatments, which are separated temporally by a lengthier healing period, may be needed for a successful treatment that supplies the desired cosmetic effect.

The vibration devices 76, 140 are functional during the treatment procedure for vibrating the treatment tip 14 and, in particular, for vibrating the portion 130 of the treatment electrode 24 contacting the skin surface 34 and overlying the region of the tissue 32 being heated by the high frequency energy. The vibration may be continuous or may be triggered to occur only when the activation button 36 is actuated. For example, the vibration devices 76, 140 may be activated for the same time period over which energy delivery occurs or for a different time period that is either shorter or longer. For example, the mechanical vibrations may be initiated after the electromagnetic energy delivery is initiated and persist through the remainder of the energy delivery, as well as continue for a given time after energy delivery ceases. The vibration devices 76, 140 may be activated to transfer mechanical vibrations through the skin surface 34 to the tissue 32 before, during, and/or after the delivery of the electromagnetic energy at each grid location to cause heating in a corresponding region of the tissue 32.

The vibration of the treatment tip 14 using one of the vibration devices 76, 140 may be effective to decrease the sensation of pain experienced by the patient 20 from the delivery of electromagnetic energy during a treatment procedure. Specifically, in one aspect, the vibration is believed to operate to average the heat applied across the treatment area within each treatment site because the treatment tip 14 and, more specifically, the portion 130 of treatment electrode 24 contacting the skin surface 34 is in continuous motion roughly within the boundaries of the grid area. In contrast, the treatment electrodes of conventional treatment tips are held pressed with a constant force of contact with the skin surface 34 during the delivery of electromagnetic energy. The dynamic motion of the portion 130 of treatment electrode 24 directly contacting the skin surface 34 compensates for hot spot thermal zones of non-uniform higher temperatures, which are highly likely sources of heat pain.

Vibration of the portion 130 of the treatment electrode 24 may also operate to interfere with the ability of nerves in the treated tissue 32 to send heat-related pain signals to the brain of the patient 20. Although not wishing to be limited by theory, it is believed under the gate control theory of pain that the perception of physical pain is not a direct result of activation of nociceptors (sensory neurons or nerve endings that sends signals that cause the perception of pain in response to a potentially damaging stimulus). Instead, the perception of physical pain is modulated by interaction between neurons that transmit pain and neurons that do not transmit pain. The gate control theory of pain teaches that activation of nerves that do not transmit pain signals, such as nerves sensitive to pressure and vibration delivered by the vibration devices 76, 140, can interfere with signals from nociceptors and thereby inhibit a patient's perception of pain, such as pain arising from heating of the tissue.

The train of vibrations delivered by the vibration devices 76, 140 induces repetitive back and forth movement of the tissue 32 in the treatment area that may act to increase local blood perfusion. Increasing the local blood perfusion may in turn act to increase the temperature loading capabilities of the skin and assist in removing heat.

The treatment depth may be adjusted by, for example, programming different output parameters (i.e., high frequency currents and voltages, duration over which current is applied, etc.) for the high frequency power supplied from generator 26 to the treatment electrode 24. Cooling can be adjusted by providing a pre-treatment cooling period, a concurrent-treatment cooling period, a post-treatment cooling period, as desired, and also by controlling the temperature of the treatment tip 14 during the cooling to be, for example, either extremely cold, medium cooled, or mildly cooled, as desired. The treatment depth may also be contingent upon other variables, such as the specific type of tissue 32 involved in the treatment.

With reference to FIGS. 16-18 and 18A and in accordance with an alternative embodiment of the invention, a handpiece 200 is constructed from a housing 202 that includes a body 204, a cover 206 assembled by conventional fasteners 208 with the body 204, and an electrical/fluid interface 210 configured to be coupled with a complementary electrical/fluid interface of the treatment tip 14. The body 204 and cover 206 of the housing 202 may be fabricated by an injection molding process using a suitable polymer resin as a construction material. The body 204 and cover 206 constitute shell halves that are integrally fastened together by the fasteners 208 as an assembly.

The housing 202 encloses an interior cavity 212 bounded on one side by an interior surface of the body 204 and bounded on the other side by an interior surface of the cover 206 that confronts the interior surface of body 204. After the body 204 and cover 206 are assembled, the handpiece 200 has a smoothly contoured shape suitable for gripping and manipulation by an operator. When the handpiece 200 is gripped, the operator can maneuver the treatment tip 14 and treatment electrode 24 to a location proximate to the skin surface 34 and, typically, to place the treatment electrode 24 in a contacting relationship with the skin surface 34 for executing a treatment repetition.

A forward nose 214 of the housing 202 includes a window 216 sized for the insertion and removal of the treatment tip 14. The electrical/fluid interface 210 is disposed between the window 216 and the majority of the interior cavity 212 inside the housing 202. The treatment tip 14 is sized to be inserted through the window 216 and configured to be physically engaged with the handpiece 200, as described below. In the engaged state, the contact pads (not shown) on the substrate 30 of the treatment electrode 24 establish respective electrical contacts with complementary electrical contacts 220, such as pogo pins, carried by the electrical/fluid interface 210 of the handpiece 200. These electrical contacts 220 are electrically coupled with one or more of the conductors 22 that extend from the handpiece 200 to the generator 26 and the system controller 18. A portion of the treatment electrode 24 projecting outwardly from the nose 214 includes the portion of the substrate 30 overlying the conductor region 28 so that, when the treatment tip 14 is mechanically engaged with the handpiece 200 and the fluid and electrical connections are established, the treatment electrode 24 is exposed through the window 216.

A shallow recess 176 defined in the cover 206 of handpiece 12 has a rim that is geometrically shaped to receive a control pad 178 with an outer perimeter of similar geometrical shape. The control pad 178 includes a display 180, controls 182, 184 that scroll different operational functions of treatment apparatus 10 on the display 180, controls 186, 188 used to respectively increase and decrease the setting for the function currently on the display 180, and a control 190 to engage a setting changed using controls 182, 184, 186, 188. The display 180 may be used to display information including, but not limited to, energy delivered, tissue impedance, duration, and feedback on procedure technique. The availability of the information displayed on the display 180 may conveniently eliminate the need to display identical information at the console 16, or may duplicate information displayed at the console 16. By displaying information at the handpiece 200, the operator can focus on the procedure without diverting his attention to glance at information displayed at the console 16. In one embodiment, the display 180 at the handpiece 200 may constitute a thin, flat liquid crystal display (LCD) comprised of a light source or reflector and an arbitrary number of color or monochrome pixels arrayed in front of the light source or reflector. A driver circuit (not shown) is provided to control the operation of the display 180. A connector 174 extends through an opening in the cover 206 to provide communication between the control pad 178 and system controller 18 through the insulated and shielded conductors 22 (FIG. 1).

Various printed circuit boards 194, 195, 196, 197 are located inside the interior cavity 212. Each of the printed circuit boards 194, 195, 196, 197 carries electrical circuitry with electronic components that support the operation and functionality of the treatment apparatus 10.

The handpiece 200 includes a frame 230, a carriage 232 that is movable relative to the frame 230, and a vibrator in the representative form of a vibration device generally indicated by reference numeral 234. Spring-loaded buttons 192a,b carried by the carriage 232 engage openings 193a,b in the treatment tip 14 to mechanically attach the treatment tip 14 with the carriage 232 as an assembly. The treatment tip 14 can be removed from the handpiece 12 by disengaging the spring-loaded buttons 192a,b from the openings 193a,b and applying an axial force directed to remove the treatment tip 14 from the handpiece 12. A grooved guide 236 is fastened to the frame 230 and a guide rail 238 on the underside of the carriage 232 has opposite side edges that are engaged with the longitudinal recess in the grooved guide 236.

The vibration device 234 includes a powered actuator in the representative form of a solenoid 244 that is configured to move the carriage 232 relative to the frame 230. The solenoid 244 has an output shaft 240 that is mechanically connected with the carriage 232 through a mechanical interface 242. The solenoid 244 is operated by drive signals generated at the system controller 18 and communicated via one or more of the insulated and shielded conductors 22. When the windings of the solenoid 244 are energized, the solenoid 244 is powered to extend the output shaft 240. Extension of the output shaft 240 causes the carriage 232 to move toward the window 216 and, accordingly, the carriage 232 to move the treatment tip 14 relative to the handpiece 12 in an outward direction through the window 216.

The mechanical coupling between the guide rail 238 and the grooved guide 236 constrains motion of the carriage 232 and the treatment tip 14 to be approximately linear and normal to the plane of the window 216. However, a person having ordinary skill in the art will appreciate that the linear movement of the mass represented by the carriage 232 and the treatment tip 14 may depart from ideality and that minor x-y motion of the treatment electrode 24 within the plane of the window 216 and, thus, normal to the linear movement may be present. During use, a portion of the treatment tip 14, typically a portion of the treatment electrode 24 and most typically a portion of the substrate 30 on the opposite side of the treatment electrode 24 from the conductor region 28, in placed in contact with the skin surface 34.

As best shown in FIG. 18A, the mechanical interface 242 includes a pair of resilient members 250, 252, which are tension springs in the representative embodiment, that are attached to the output shaft 240 by an attachment structure 254 and to the carriage 232 by another attachment structure 256. The resilient members 250, 252 bridge across the gap between the end of the output shaft 240 and the carriage 232. A force sensor 258 is clipped to the carriage 232 and, therefore, rides with the carriage 232 as the carriage 232 is moved. The force sensor 258 supplies feedback on the vibration of carriage 232 and detects contact of the treatment tip 14 with the skin surface 34. A ram 260 of the mechanical interface 242 is secured to the end of the output shaft 240 of the solenoid 244. The ram 260 is disposed inside of a cylinder 262, which also encloses a cup-shaped receptacle 264 and a resilient member 266 in the representative form of a compression spring. The resilient member 266 is retained inside the cylinder 262 and is disposed between the ram 260 and the receptacle 264. A portion of the receptacle 264 contacts the force sensor 258 when the output shaft 240 is extended to move the carriage 232 relative to the frame 230. The extension pushes the carriage 232 toward the window 216 in a direction away from the stationary solenoid 244 and compresses the resilient member 266.

The force sensor 258 supplies feedback to the system controller 18 on the variation in the contact force between the treatment tip 14 and the skin surface 34. For example, the force of contact between the treatment tip 14 and the skin surface 34 may be less than one kilogram (e.g., 0.35 kg) and, when the mechanical vibrations are initiated, the force of contact may change (±100%) as the carriage 232 and the treatment tip 14 move axially relative to the skin surface 34.

When power is removed from the windings of the solenoid 244, the resilient members 250, 252 cooperate to supply a spring bias that shifts the carriage 232 in a direction away from the window 216. A first magnet 267 is secured to the output shaft 240 of the solenoid 244 and a second magnet 268 is held by the frame 230. The first magnet 267 moves with the output shaft 240 relative to the second magnet 268, which remains stationary. The resilient members 250, 252 are assisted in shifting the carriage 232 by a magnetic force of attraction between the first and second magnets 267, 268. In one embodiment, the magnets 267, 268 are composed of a material, such as a ferromagnetic material, that is permanently magnetized. The first and second magnets 267, 268 supply a functional hard stop to the rearward motion of the output shaft 240.

Figure 21:
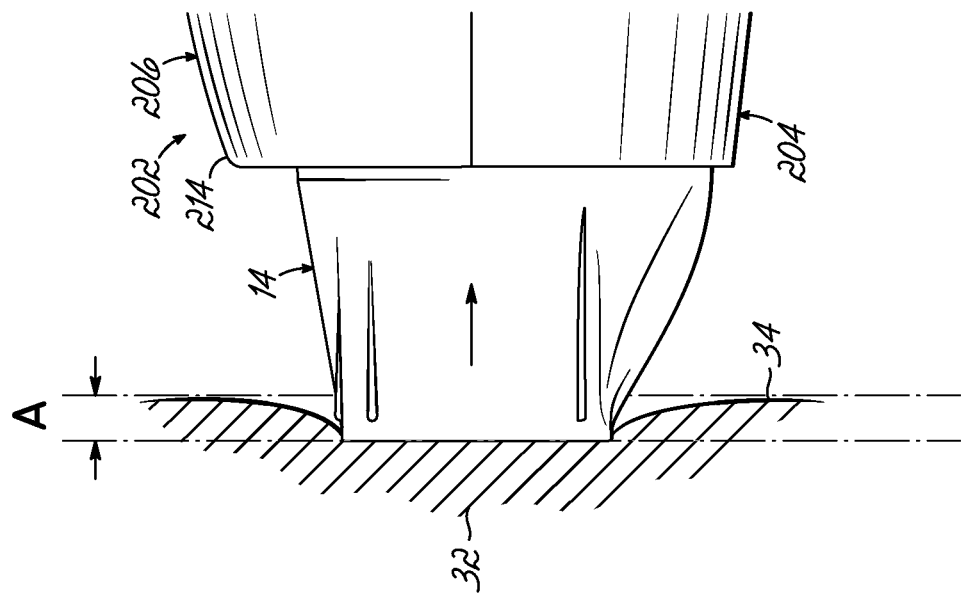
FIGS. 21 and 22 are detailed views similar to FIGS. 9 and 15 of the treatment tip in use during a treatment procedure conducted using the treatment system of FIGS. 1 and 16-20.
Figure 22:
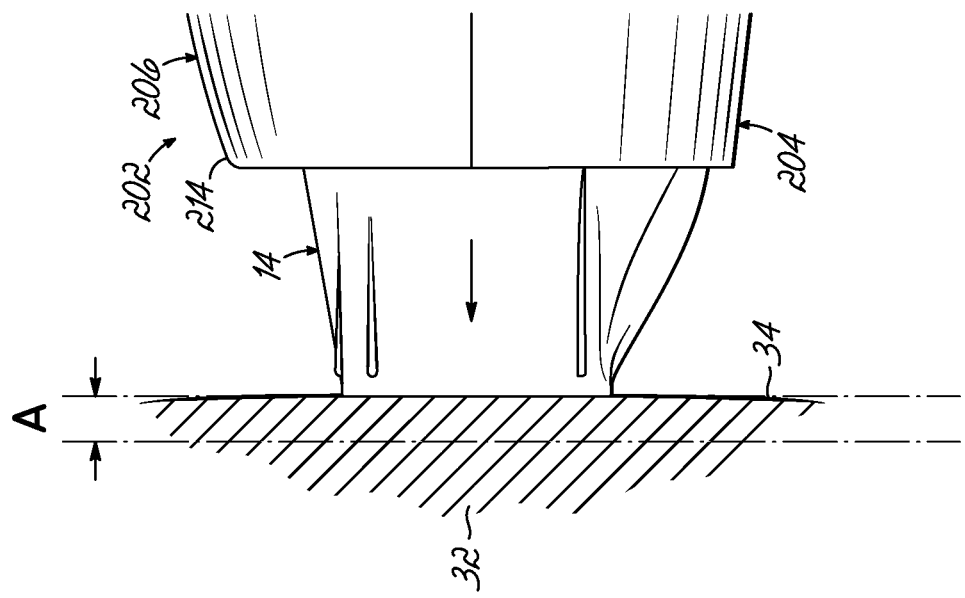

The alternately back and forth movement of the carriage 232 may be implemented in response to powering the treatment electrode 24 during a treatment procedure. The forced motion of the carriage 232 by operation of the solenoid 244 moves the treatment tip 14, which is mechanically connected with the carriage 232 and moves as a unit with the carriage 232, from an initial position, as best shown in FIG. 18, toward the skin surface 34. The forward end of the treatment tip 14, which carries treatment element 24, applies a force vector directed primarily inward to the skin surface 34. When the output shaft 240 is fully extended, the forward motion of the treatment tip 14 and carriage 232 halts, as shown in FIGS. 19, 19A. This inwardly directed force depresses the skin surface 34 over a shallow amplitude, A, as best shown in FIG. 21, that represents the extension of the carriage 232 and the treatment tip 14. The tissue 32 applies a counterforce that resists the inwardly directed force from the treatment tip 14 but that yields slightly to permit the skin surface 34 to be depressed.

When the solenoid 244 is de-energized, the force applied by the output shaft 240 is removed from the carriage 232 and treatment tip 14. An attractive force acting between the magnets 267, 268 causes the output shaft 240 to initially lose contact with the carriage 232, as best shown in FIG. 19A. The output shaft 240 is induced to move to a fully retracted position shown in FIG. 20. The resilient members 250, 252 are extended by this motion of the output shaft 240, which in turn applies a return force to the carriage 232. The return force transferred from the resilient members 250, 252 to the carriage 232 causes the carriage 232 to rapidly return the initial position of FIG. 18 and the resilient members 250, 252 to return to their initial position of FIGS. 18, 18A. This retracts the treatment tip 14 from the skin surface 34. Because the clinician is gripping the handpiece 12 and pressing the treatment tip 14 toward the skin surface 34, contact is maintained between the treatment electrode 24 and the skin surface 34 as the treatment tip 14 is vibrated by the vibration device 234.

The rapid repetition of this movement sequence imparts a series of mechanical vibrations to and through the skin surface 34 that propagate into the underlying tissue 32 as mechanical vibration waves. In various embodiments, the vibration frequency may be on the order of 20 Hz to 80 Hz and the amplitude, A, may be on the order of 1 mm to 6 mm. The alternation in the direction of motion of the carriage 232 gives rise to reciprocating movement of the treatment tip 14 and the portion of the treatment tip 14 contacting the skin surface 34.

The solenoid 244 of the vibration device 234 is coupled by ring-shaped vibration dampers 270, 272 with a recessed groove defined in the frame 230 and another recessed groove defined in an air flow deflector 274 partially surrounding the exterior of the solenoid 244. The vibration dampers 270, 272 may be composed of a relatively soft durometer elastomeric material like a silicone rubber. The vibration dampers 270, 272 are axially spaced apart at different locations along the length of the solenoid 244. The vibration dampers 270, 272 supply a mechanical connection between the housing 202 and the solenoid 244 of the vibration device 234, but operate to attenuate the transfer of vibration from the solenoid 244.

The solenoid 244 is cooled by a forced air flow from a blower or fan 276. The air flow from the fan 276 is directed about the exterior of the solenoid 244 by the air flow deflector 274, which is separated from outside case of the solenoid 244 by a gap. The solenoid 244 generates heat when powered. The force flow of air extracts heat from the solenoid 244, which is cooled and, therefore, has a lower operating temperature than in the absence of active cooling. The housing 202 includes ventilation openings (not shown) communicating with the interior cavity 212 and that cooperate with the fan 276 to intake air at ambient temperature and to exhaust air warmed in excess of ambient temperature by the heat generated by solenoid 244.

An activation button 280, which is accessible to the operator from the exterior of the handpiece 12, is configured to be actuated to actuate a switch 282 that closes a normally open circuit to connect the treatment electrode 24 with the generator 26. The closed circuit energizes the treatment electrode 24 with power supplied to the handpiece 12 from the generator 26 and also electrically powers the solenoid 244 of the vibration device 234 to prompt the transfer of mechanical vibrations to the skin surface 34. Consequently, actuation of the activation button 280 triggers delivery of the high frequency energy and the delivery of mechanical vibrations over a timed delivery cycle to the target tissue 32.

The timing of the mechanical vibration delivery with respect to the electromagnetic energy delivery is selected according to the specific treatment procedure, and may be orchestrated under the control of the system controller 18 at the console 16. Various delivery profiles for the electromagnetic energy and the mechanical vibrations may be developed for different types of patient treatments. In one embodiment, the onset of mechanical vibrations is delayed in time until after the energy delivery is initiated. In one embodiment, the mechanical vibrations are continued for a given time after energy delivery concludes. In other embodiments, the onset and/or end of the mechanical vibrations may coincide with the onset and end of energy delivery.

Figure 23:
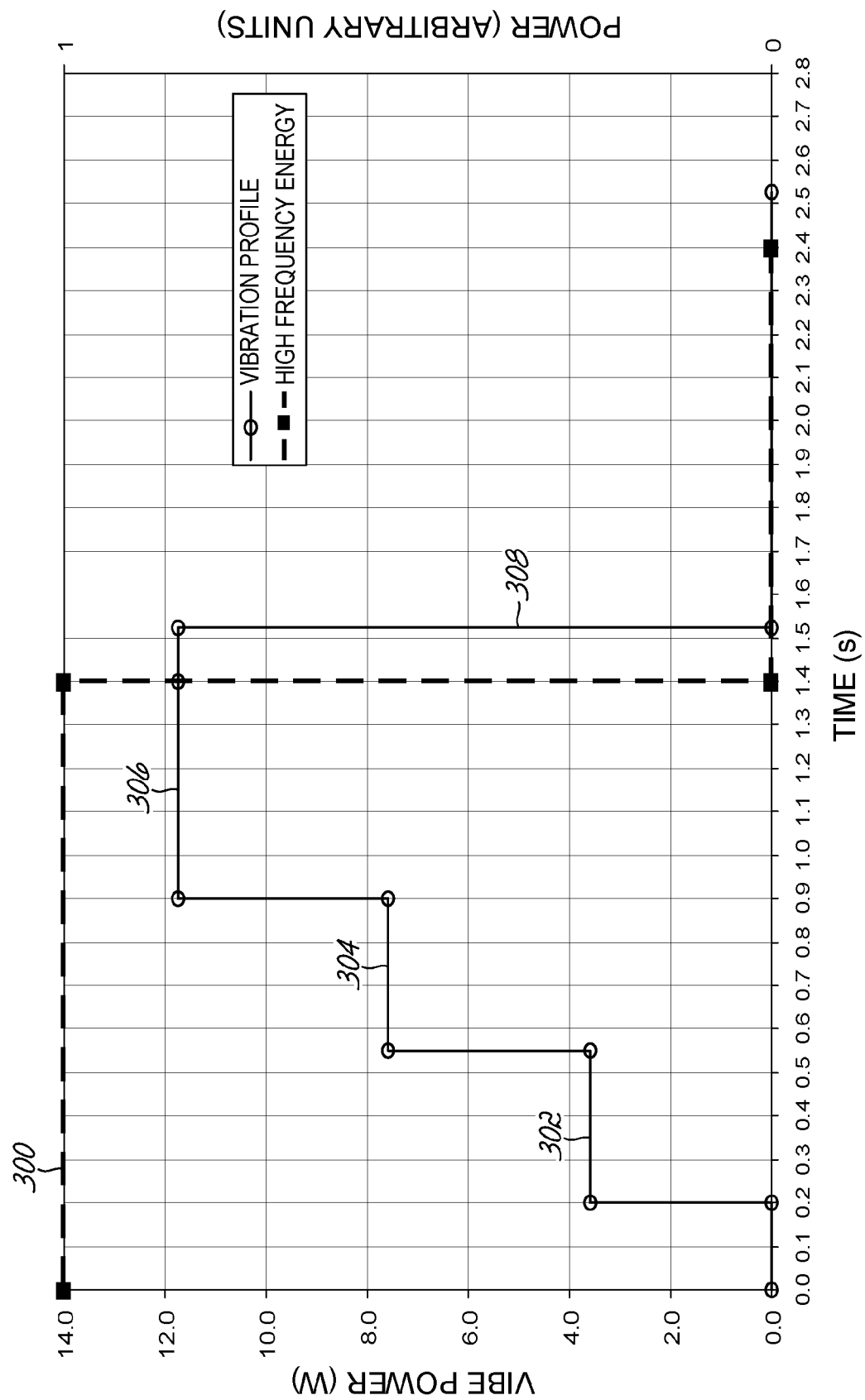
FIG. 23 is a diagrammatic view illustrating a stepped-amplitude protocol for vibration to provide functional mechanical stimulation when delivering high frequency energy from the treatment electrode to the patient's tissue.

With reference to FIG. 23, an exemplary delivery profile for high frequency power and vibration as a function of time to the tissue 32 is illustrated. The vibration profile may be used to operate vibration device 234 (FIGS. 16-22) or, alternatively, to operate either the vibration device 234 (FIGS. 1-9) or the vibration device 234 (FIGS. 10-15).

In the specific delivery profile, high frequency power is delivered in a pulse initiating at a time of 0.0 seconds (the origin of the x-axis) and with the treatment electrode 24 in a contacting relationship with the skin surface 34 to promote energy transfer, as well as the subsequent vibration transfer. The delivery of the high frequency power is indicated diagrammatically by line 300. Power delivery may be preceded by a pulse of coolant to cool the tissue 32 inwardly from the skin surface 34.

Mechanical vibrations are initiated subsequent to the initiation of power delivery, for example at a time of 0.2 seconds after the delivery of electromagnetic power is initiated. While electromagnetic power is delivered from the treatment electrode 24, the power of the mechanical vibration is increased with increasing time. Over an interval of 0.35 seconds (from 0.2 seconds to 0.55 seconds), the solenoid 244 is energized at a first power level, as indicated by line 302, and held constant at the first power level to deliver mechanical vibrations with a first amplitude and/or frequency and in a direction primarily perpendicular to the skin surface 34.

At a future time (e.g., 0.55 seconds after the initiation of electromagnetic power delivery), the power to the solenoid 244 is increased to a second power level, as indicated by line 304, to establish mechanical vibrations with a second amplitude and/or frequency greater than the first amplitude and/or frequency. The power is held constant at the second power level 304 to deliver mechanical vibrations at the second amplitude and/or frequency. Vibration at the second amplitude and/or frequency of level 304 is sustained over an interval of, for example, 0.35 seconds (from 0.55 seconds to 0.9 seconds).

At a more advanced time into the future (e.g., 0.9 seconds after the initiation of electromagnetic power delivery), the power to the solenoid 244 is again increased to a third power level, as indicated by line 306, to deliver mechanical vibrations with a third amplitude and/or frequency greater than the second amplitude and/or frequency. The power is held constant at the third power level 306 to deliver mechanical vibrations at the third amplitude and/or frequency. Vibration is sustained at the third amplitude and/or frequency of the third power level 306 over an interval of, for example, 0.63 seconds (from 0.9 seconds to 1.53 seconds). The delivery of high frequency electromagnetic energy is discontinued (e.g., after a treatment time of 1.4 seconds) before the mechanical vibrations are discontinued, as indicated by line 308, a short time (e.g., a little over one millisecond) thereafter. As a result, the mechanical vibrations continue after power delivery in the pulse of high frequency power 300 concludes.

Preferred vibration power for the mechanical vibrations is between 1 watt and 30 watts, preferably between 2 watts and 20 watts, more preferably between 2 watts and 12 watts, and most preferably between 3 watts and 12 watts.

A person having ordinary skill in the art will appreciate that the vibration profile in FIG. 23 is merely exemplary and that the number of different vibration levels and the amplitude and duration of each vibration level may differ from the exemplary vibration profile. The vibration profile may be adjusted to provide functional mechanical stimulation to accommodate varying nerve densities in different tissue types and different levels of patient skin laxity and thereby provide a suitable measure of pain relief to the patient.

Figure 24:
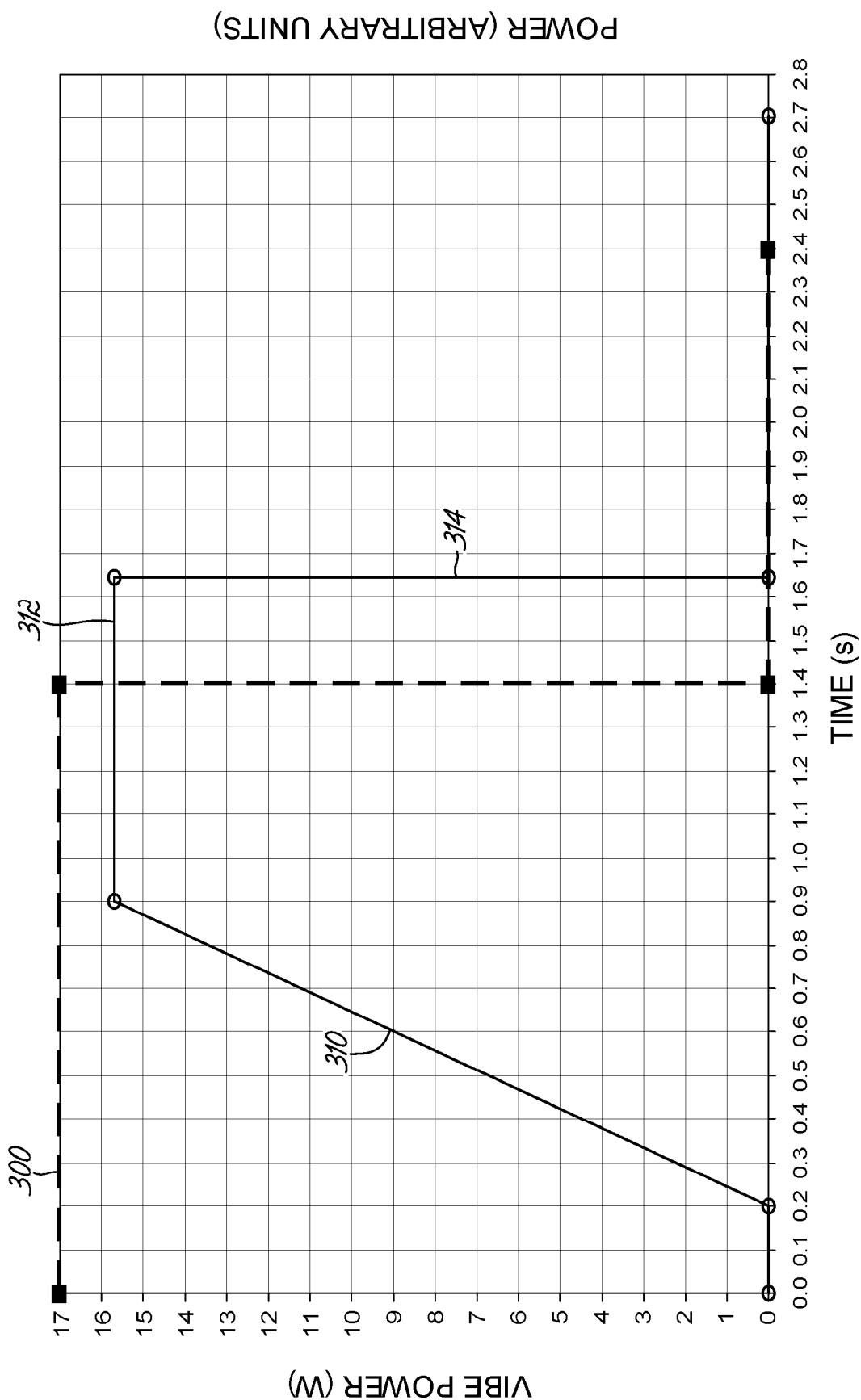
FIG. 24 is a diagrammatic view illustrating a ramped protocol for vibration to provide functional mechanical stimulation when delivering high frequency energy from the treatment electrode to the patient's tissue.

With reference to FIG. 24 in which like reference numerals refer to like features in FIG. 23 and in accordance with an alternative embodiment, another exemplary profile for high frequency power delivery and vibration delivery as a function of time to the tissue 32 is illustrated. The vibration profile may be used to operate vibration device 234 (FIGS. 16-22) or, alternatively, either the vibration device 234 (FIGS. 1-9) or the vibration device 234 (FIGS. 10-15). The ramping of the vibration level in the profile of FIG. 23 contrasts with the abrupt changes in vibration level exhibited in the profile of FIG. 22.

Mechanical vibrations are initiated after electromagnetic energy delivery is initiated, for example at a time of 0.2 seconds after the delivery of electromagnetic power is initiated. While electromagnetic power is being delivered, the power of the mechanical vibration is increased with increasing time. Specifically, the solenoid 244 is energized at, for example, 0.2 seconds and the vibration power is ramped upwardly at a given rate over an interval spanning, for example, from 0.2 seconds to 0.9 seconds, as indicated by line 310, to deliver mechanical vibrations with increasing amplitude and/or frequency. In the representative embodiment, the vibration power is linearly ramped at a constant rate to a maximum vibration power (e.g., 15.7 Watts), at which point the maximum vibration power is sustained to provide an approximately continuous delivery of mechanical vibrations during the remainder of the electromagnetic energy delivery, as indicated by line 312. At a given time (e.g., 0.25 seconds), the delivery of electromagnetic energy is discontinued, and the power to the solenoid 244 is switched off and the mechanical vibrations cease, as indicated by line 314. In the representative embodiment, the cessation of mechanical vibration occurs after the delivery of electromagnetic energy is discontinued.

References herein to terms such as "vertical", "horizontal", etc. are made by way of example, and not by way of limitation, to establish a frame of reference. It is understood that various other frames of reference may be employed for describing the invention without departing from the spirit and scope of the invention. It is also understood that features of the invention are not necessarily shown to scale in the drawings. Furthermore, to the extent that the terms "composed of", "includes", "having", "has", "with", or variants thereof are used in either the detailed description or the claims, such terms are intended to be inclusive and open-ended in a manner similar to the term "comprising".

It will be understood that when an element is described as being "attached", "connected", or "coupled" to another element, it can be directly connected or coupled to the other element or intervening elements may be present. In contrast, when an element is described as being "directly attached", "directly connected", or "directly coupled" to another element, there are no intervening elements present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicants' general inventive concept.

What is claimed is:

1. A tissue treatment apparatus for use in treating a region of tissue located beneath a skin surface with electromagnetic energy, the tissue treatment apparatus comprising:
    a housing;
    a frame coupled with the housing, the frame having a first coupling element;
    a carriage including a second coupling element connected with the first coupling element of the frame, the carriage constrained by the connection between the first and second coupling elements to move linearly relative to the housing and the frame;
    a delivery device mechanically coupled with the carriage, the delivery device including a treatment tip configured to transfer the electromagnetic energy through the skin surface to the region of tissue, the treatment tip having a portion configured to contact the skin surface; and
    a vibration device mechanically coupled by the carriage with the treatment tip, the vibration device configured to transfer mechanical vibrations from the portion of the treatment tip to the skin surface by moving the carriage and the treatment tip linearly relative to the housing and the frame.

2. The tissue treatment apparatus of claim 1 wherein the housing, the vibration device, and the carriage comprise components of a handpiece and the treatment tip is removably connected with the handpiece.

3. The tissue treatment apparatus of claim 1 wherein the vibration device is configured to power the movement of the treatment tip at a power between 2 watts and 12 watts.

4. The tissue treatment apparatus of claim 1 wherein the vibration device is configured to move the treatment tip at a frequency between 20 Hz and 80 Hz.

5. The tissue treatment apparatus of claim 1 wherein the housing has an interior cavity, the carriage is disposed within the interior cavity, and the carriage is configured to move within the interior cavity relative to the housing.

6. The tissue treatment apparatus of claim 1 wherein the vibration device includes a solenoid supported by the frame, the solenoid configured with an output shaft that is mechanically coupled by the carriage with the treatment tip, and the output shaft of the solenoid configured to move the treatment tip in opposite first and second directions relative to the housing and the frame to generate the mechanical vibrations.

7. The tissue treatment apparatus of claim 6 wherein the output shaft is oriented to move the treatment tip toward the skin surface, and further comprising:
    a resilient member coupling the carriage with the solenoid, the resilient member applying a spring biasing force opposite to the first direction in which the output shaft of the solenoid moves the treatment tip relative to the skin surface; and
    a vibration damper coupling the solenoid with the frame.

8. The tissue treatment apparatus of claim 6 further comprising:
    a first magnet coupled with the output shaft; and
    a second magnet coupled with the frame, the second magnet arranged relative to the first magnet such that an attractive force is applied between the first and second magnets.

9. The tissue treatment apparatus of claim 1 further comprising:
    a blower inside the housing, the blower configured to direct a forced air flow over the vibration device to cool the vibration device.

10. The tissue treatment apparatus of claim 1 wherein the vibration device is configured to vibrate the treatment tip in a direction primarily perpendicular to a surface normal of the skin surface.

11. The tissue treatment apparatus of claim 1 wherein the first coupling element is grooved guide and the second coupling element is a guide rail engaged with the grooved guide.

* * * * *

UNITED STATES PATENT AND TRADEMARK OFFICE
CERTIFICATE OF CORRECTION

| | | |
|---|---|---|
| PATENT NO. | : 8,506,506 B2 | Page 1 of 1 |
| APPLICATION NO. | : 12/649781 | |
| DATED | : August 13, 2013 | |
| INVENTOR(S) | : Dragan D. Nebrigic et al. | |

It is certified that error appears in the above-identified patent and that said Letters Patent is hereby corrected as shown below:

Title Page 2, Item (56), in Other Publications, second to the last line, change "pteient" to --patient--.

In the Specifications:

At column 2, line number 24, after "skin" insert --.--.

At column 10, line number 59, change "fully" to --full--.

At column 11, line number 17, after "and" delete "causes".

At column 16, line number 7, after "skin" insert --.--.

At column 19, line number 29, change "in" to --is--.

At column 20, line number 39, after "return" insert --to--.

At column 23, line number 39, change "applicant" to --Applicants--.

In the Claims:

At column 24, claim number 11, line number 58, after "is" insert --a--.

Signed and Sealed this
Nineteenth Day of November, 2013

Teresa Stanek Rea
*Deputy Director of the United States Patent and Trademark Office*